(12) United States Patent
Hawkins

(10) Patent No.: US 6,451,530 B1
(45) Date of Patent: Sep. 17, 2002

(54) FLUORESCENT NUCLEOTIDE ANALOG HAIRPIN FORMATION FOR DETECTION OF NUCLEIC ACID HYBRIDIZATION

(75) Inventor: Mary Hawkins, Potomac, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/319,648

(22) PCT Filed: Dec. 10, 1997

(86) PCT No.: PCT/US97/22448

§ 371 (c)(1),
(2), (4) Date: Jul. 30, 1999

(87) PCT Pub. No.: WO98/26093

PCT Pub. Date: Jun. 18, 1998

Related U.S. Application Data

(60) Provisional application No. 60/032,844, filed on Dec. 13, 1996.

(51) Int. Cl.[7] ............ C12Q 1/68; C12N 15/11; C12N 15/63
(52) U.S. Cl. ............ 435/6; 435/91.2; 536/23.1; 536/24.3
(58) Field of Search ............ 435/6, 91.2; 536/23.1, 536/24.3

(56) References Cited

U.S. PATENT DOCUMENTS 5,525,711 A 6/1996 Hawkins et al.
5,928,862 A * 7/1999 Morrison ............ 435/6

FOREIGN PATENT DOCUMENTS

EP 0 601 889 A2 6/1994
WO WO 92/18650 10/1992

* cited by examiner

Primary Examiner—John S. Brusca
(74) Attorney, Agent, or Firm—Townsend and Townsend and Crew, LLP

(57) ABSTRACT

This invention provides methods and compositions for the detection of nucleic acid interactions with other nucleic acids or with proteins. The methods generally utilize a nucleic acid (e.g., an oligonucleotide) that contains one or more fluorescent nucleotide analogues. The fluorescence of the nucleotide analogues is quenched (reduced) when they are incorporated into the oligonucleotide. Alteration of the normal conformation of the oligonucleotide by hybridization (e.g. to form a loop) or by protein binding reduces and/or eliminates the quench thereby causing a detectable increase in fluorescence.

35 Claims, 3 Drawing Sheets nMyc gene

```
   1 agctccgagc ccccgagctg ggtcacggag atgctgcttg agaacgagct gtggggcagc
  61 ccggccgagg aggacgcgtt cggcctgggg ggactgggtg gcctcacccc caacccggtc
 121 atcctccagg actgcatgtg gagcggcttc tccgcccgcg agaagctgga gcgcgccgtg
 181 agcgagaagc tgcagcacgg ccgcgggccg ccaaccgccg gttccaccgc ccagtccccg
 241 ggagccggcg ccgccagccc tgcgggtcgc gggcacggcg gggctgcggg agccggccgc
 301 gccggggccg ccctgcccgc cgagctcgcc caccggccg ccgagtgcgt ggatcccgcc
 361 gtggtcttcc cctttcccgt gaacaagcgc gagccagcgc ccgtgcccgc agccccggcc
 421 agtgccccgg cggcgggccc tgcggtcgcc tcggggcgg gtattgccgc cccagccggg
 481 gccccggggg tcgcccctcc gcgcccaggc ggccgccaga ccagcggcgg cgaccacaag
 541 gccctcagta cctccggaga ggacaccctg agcgattcag atgatgaaga tgatgaagag
 601 gaagatgaag aggaagaaat cgacgtggtc actgtggaga gcggcgttc ctcctccaac
 661 accaaggctg tcaccacatt caccatcact gtgcgtccca agaacgcagc cctgggtccc
 721 gggagggctc agtccagcga gctgatcctc aaacgatgcc ttcccatcca ccagcagcac
 781 aactatgccg ccccctcccc ctacgtggag agtgaggatg cacccccaca gaagaagata
 841 aagagcgagg cgtccccacg tccgctcaag agtgtcatcc cccaaaggc taaaggūcttū
 901 <u>agcccccgaa actctgactc cū</u>ūaggacagt gagcgtcgca gaaaccacaa catcctggag
 961 cgccagcgcc gcaacgacct tcggtccagc tttctcacgc tcagggacca cgtgccggag
1021 ttggtaaaga atgagaaggc cgccaaggtg gtcattttga aaaggccac tgagtatgtc
1081 cactccctcc aggccgagga gcaccagctt ttgctggaaa aggaaaaatt gcaggcaaga
1141 cagcagcagt tgctaaagaa aattgaacac gctcggactt gctagacgct tctcaaaact
1201 ggacagtcac tgccactttg cacattttga ttttttttt aaacaaacat tgtgttgaca
1261 ttaagaatgt tggtttactt tcaa
```

FLUORESCENT NUCLEOTIDE ANALOG HAIRPIN FORMATION FOR DETECTION OF NUCLEIC ACID HYBRIDIZATION

CROSS-REFERENCE TO RELATED APPLICATIONS

This application claims the benefit of U.S. Ser. No. 60/032,844 filed on Dec. 13, 1996.

FIELD OF THE INVENTION

This invention relates to methods of detecting hybridization between nucleic acids or protein/nucleic acid interactions. In particular this invention pertains to nucleic acid probes containing a fluorescent nucleotide analogue whose fluorescence level increases when the probe hybridizes to a target nucleic acid or when the probe is bound by a protein.

BACKGROUND OF THE INVENTION

One of the most specific molecular recognition events takes place when a strand of nucleic acid anneals (hybridizes) to its complement. A single-stranded oligonucleotide probe can find a complementary strand in the presence of a large excess of other nucleic acids. This process has facilitated the exploration of gene structure and organization, the measurement of gene expression and function, and the detection and characterization of a wide variety of pathologies.

Hybridization based assays typically require detection and/or quantification of a hybrid duplex formed between a probe nucleic acid and its corresponding target nucleic acid. However, because the measurable changes in the physical properties of nucleic acids that occur upon hybridization are rather small, such assays most frequently utilize labels attached either to the nucleic acid probes or to the target nucleic acids to detect the hybrid duplexes. After hybridization, typically the hybridized nucleic acids are immobilized (e.g., attached to a membrane) and the unhybridized nucleic acids are washed away. The immobilized label is then detected and/or quantitated to provide a measure of the hybrid duplex.

The requirement that unhybridized probes be separated from hybridized probes precludes the use of hybridization for real-time monitoring of nucleic acid syntheses or protein-nucleic acid interactions or for location specific nucleic acids in living cells. In addition, the need to immobilize hybrids on a solid surface limits sensitivity, since probes bind non-specifically to surfaces. While several schemes have been put forward for detecting specific nucleic acids in homogeneous solutions (see, e.g., Heller et al. European Patent Application 82303699.1, Morrison et al. (1989) *Anal. Biochem.*, 183: 231–244, Cardullo et al. (1988) *Proc. Natl. Acad. Sci. USA*, 85: 8790–8794, Morrison et al. (1993) *Biochem.*, 32: 3095–3104, and Sixou et al. (1994) *Nucl. Acids Res.*, 22: 662–668), these methods are typically unsuitable for real-time measurements or use in living cells.

Newer approaches for the detection of nucleic acid hybridizations and protein-nucleic acid interactions typically rely on energy transfer between a fluorophore and a quencher molecule or a second fluorophore (e.g., a fluorescence resonance energy transfer system). Thus, for example, a lumazine derivative has been used in conjunction with a bathophenanthroline-ruthenium complex as an energy transfer system in which the lumazine derivative acted as an energy donor and the ruthenium complex acted as an energy receptor. The lumazine derivative and ruthenium complex were attached to different nucleic acids. Energy transfer occurred when the two compounds were brought into proximity resulting in fluorescence. The system provided a mechanism for studying the interaction of molecules bearing the two groups (see, e.g., Bannwarth et al., *Helvetica Chimica Acta.* (1991) 74: 1991–1999, Bannwarth et al. (1991), *Helvetica Chimica Acta.* 74: 2000–2007, and Bannwarth et al., European Patent Application No. 0439036A2).

Another approach utilizes nucleic acid probes bearing a fluorophore and a quencher molecule. The probes were self-complementary and adopted a hairpin conformation in solution. The hairpin juxtaposed the fluorophore and the quencher thereby reducing or eliminating fluorescence of the fluorophore. When the probes hybridized to a target nucleic acid, they linearized, separating the fluorophore from the quencher molecule and thereby providing a fluorescent signal (see Tyagi and Kramer et al. (1996) *Nature Biotechnology*, 14: 303–308).

Both of these approaches required a fluorescent compound and a second fluorophore or a quencher. Most fluorescent compounds, however, generally suffer the disadvantage that the fluorescent complexes and their binding moieties are relatively large. The presence of large fluorescent labels and associated linkers may alter the mobility of the nucleic acid, either through a gel as in sequencing, or through various compartments of a cell.

In addition, the presence of these markers alters the interaction of the labeled nucleic acid with other molecules either through chemical interactions or through steric hindrance. The presence of these markers thus makes it difficult to study the interactions of DNA with other molecules such as other nucleic acids or proteins.

SUMMARY OF THE INVENTION

This invention provides new methods and compositions for the detection of nucleic acid interactions with other nucleic acids or with proteins. The methods and compositions utilize fluorescent nucleotide analogs as fluorescent moieties and thus do not suffer from the limitations described above.

The methods of this invention generally utilize a nucleic acid (e.g., an oligonucleotide) that contains one or more fluorescent nucleotide analogues. The fluorescence of the nucleotide analogues is quenched (reduced) when they are incorporated into the oligonucleotide (see, e.g., U.S. Pat. No. 5,525,711 and Hawkins et al. (1995) *Nucl. Acids Res.*, 23: 2872–2880. However, when the fluorescent nucleotide analogue is removed from the quenching influence of neighboring bases (e.g, present in a loop) fluorescence activity is partially or completely restored. Without being bound by a particular theory, it is believed that alteration of the normal conformation (e.g., base stacking) of the oligonucleotide at the location of the fluorescent nucleotide analogue reduces and/or eliminates the quench thereby causing an increase in fluorescence.

Thus, in one embodiment, this invention provides methods of detecting the presence, absence, or quantity of a target nucleic acid. The methods involve contacting the target nucleic acid with a nucleic acid probe where the nucleic acid probe comprises a fluorescent nucleotide located in the probe such that, when the probe hybridizes to the target nucleic acid, the fluorescent nucleotide is present in a loop that does not participate in complementary base pairing with a nucleotide of the target nucleic acid; and detecting the fluorescence produced by the fluorescent nucleotide, when said probe forms a hybrid duplex with said target nucleic acid. In one preferred embodiment, the loop ranges in length from about 1 to about 100 nucleotides when the probe hybridizes to said target nucleic acid. In particularly preferred probes, the loop is an insertion in said nucleic acid probe which is otherwise complementary to said target nucleic acid or to a contiguous subsequence of said target nucleic acid. In some preferred embodiments, the insertion is three nucleotides in length and comprises two nucleotides each adjacent to the fluorescent nucleotide. In particularly preferred embodiments, at least one nucleotide adjacent to the fluorescent nucleotide is a purine (e.g., adenosine), and in still more preferred embodiments, the fluorescent nucleotide is bordered by at least two adjacent purines (e.g., adenosine) in both the 5' and 3' direction. In a most preferred embodiment, the insertion is a single base insertion; the fluorescent nucleotide.

In yet another embodiment, the insertion is self-complementary and forms a hairpin in which the fluorescent nucleotide is present in the loop of said hairpin and does not participate in complementary base pairing. The nucleotides comprising the loop can be selected such that they are not complementary to the corresponding nucleotides of the target nucleic acid when said probe is hybridized to said target nucleic acid and where said probe is complementary to at least two non-contiguous subsequences of said target nucleic acid.

In another embodiment, the fluorescent nucleotide is present in a terminal subsequence of the nucleic acid probe where the terminal subsequence does not hybridize to the target nucleic acid when the remainder of said nucleic acid probe hybridizes to said target nucleic acid. The terminal subsequence may form a terminal hairpin by hybridization with a second subsequence of the probe such that the fluorescent nucleotide is present in a loop of said hairpin and does not participate in complementary base pairing.

Particularly preferred detection methods involve detecting an increase in fluorescence of the fluorescent nucleotide when the probe forms a hybrid duplex with the target nucleic acid. In preferred label oligonucleotides, the fluorescent nucleotides include one or more of any of the fluorescent nucleotide analogues described herein.

In another embodiment, this invention provides methods of amplifying nucleic acids. The methods involve providing in a nucleic acid amplification mixture a label oligonucleotide comprising a fluorescent nucleotide analog, where the label oligonucleotide comprises a nucleotide sequence such that when an amplification product is formed in a nucleic acid amplification reaction using the mixture, the label oligonucleotide hybridizes to the amplification product or to a subsequence thereof and forms a loop in which said fluorescent nucleotide analogue does not participate in complementary base pairing. The hybridization of the label oligonucleotide to the amplification product produces a change in fluorescence that is detected. The label oligonucleotide can be a primer in the amplification reaction or it can be a separate label that does not act as a primer in the amplification reaction. The label oligonucleotide can include any of the above-described probes or label oligonucleotides described herein.

In still yet another embodiment, this invention provides fluorescent labels. The labels comprising any of the probes or label oligonucleotides described herein hybridized to a target nucleic acid forming a hybrid duplex in which said fluorescent nucleotide does not participate in complementary base pairing with a nucleotide of said target nucleic acid.

It was also a discovery of this invention that the signal produced by a label oligonucleotide hybridizing in a complex mixture of nucleic acids can be improved by cutting (e.g., by shearing, acid hydrolyzing, or restriction digesting) the other nucleic acids (e.g, target, template, or other nucleic acids present in a sample) to a characteristic length and/or by providing an overabundance of the label oligonucleotide. This cutting step can be practiced in any of the methods described herein. The cutting alters hybridization kinetics to favor binding by the label oligonucleotide. While cutting to any shorter length improves label oligonucleotide binding so long as the target nucleic acid is not destroyed, in a preferred embodiment, the nucleic acids are cut to a length that substantially approximates the length of the target nucleic acid(s) (e.g., to a length no greater than 20 times, preferably no greater than 10 times, more preferably to a length no greater than 5 times, and most preferably to a length no greater than 2 times, 1.5 times or even no greater than 1 times the length of the label oligonucleotide). In a most preferred embodiment, the characteristic length is approximately the length of the label oligonucleotide.

This invention also provides nucleic acid amplification mixtures comprising a label oligonucleotide and a DNA polymerase, wherein said label oligonucleotide comprises a fluorescent nucleotide analog and has a nucleotide sequence such that when an amplification product is formed in a nucleic acid amplification reaction using the amplification mixture, the label oligonucleotide hybridizes to the amplification product or to a subsequence thereof and forms a loop in which said fluorescent nucleotide analogue does not participate in complementary base pairing. Again, the label oligonucleotide can be any of the probes or label oligonucleotides described herein.

This invention also provides kits for performing nucleic acid amplifications or for detecting the presence absence or quantity of a nucleic acid in a sample. The kits comprise a container containing any of the probes or label oligonucleotides described herein. The kit can further comprise, one or more restriction enzymes, a buffer, and/or any of the other reagents useful for practicing the method to which the kit is directed.

DEFINITIONS

The terms "nucleotide" or "nucleotide monomer", as used herein, refer to the "standard" nucleotides; adenosine, guanosine, cytidine, thymidine, and uracil, or derivatives of these nucleotides. Such derivatives include, but are not limited to, inosine, 5-bromodeoxycytidine, 5-bromo-deoxyuridine, $N^6$-methyl-deoxyadenosine and 5-methyl-deoxycytidine. The terms also include nucleotide analogues, more preferably fluorescent nucleotide analogues including, but not limited to 2-amino purine, any of the pteridine nucleotides disclosed herein, or any of the other fluorescent nucleotides disclosed herein.

A "fluorescent nucleotide" or a "fluorescent nucleotide analogue" refers to a nucleotide or nucleotide analogue that is capable of emitting a fluorescent signal when illuminated with light of an appropriate wavelength. The fluorescent signal is reduced or eliminated when the nucleotide is incorporated into an oligonucleotide. However, as long as the nucleotide analogue emits a fluorescent signal with a quantum yield above 0.04, more preferably above 0.1 and most preferably above 0.15 when it exists as a monomer in an aqueous solution it is regarded as a fluorescent nucleotide.

A "pteridine nucleotide" or a "lumazine nucleotide" refer to fluorescent nucleotide analogues in which the base portion of the molecule is a pteridine/pteridine derivative or a lumazine/lumazine derivative respectively. It is recognized that lumazines are a subclass of pteridines.

The term "fluorescence intensity" refers to the quantum yield of a molecule. Quantum yield is typically expressed as a relative quantum yield (relative to a standard) and is given as:

$$Q = \frac{Q_{std}\left(\frac{\int Em_{std}}{Abs_{std}}\right)}{\frac{\int Em_{Sample}}{Abs_{Sample}}}$$

where $Q_{std}$ is the quantum yield of a standard $EM_{std}$ is the emission of a standard, $ABS_{std}$ is the absorbance of a standard $EM_{sample}$ is the emission of a sample, and $ABS_{sample}$ is the absorbance of a standard. In a preferred embodiment, the standard is quinine sulfate (QS) which has a quantum yield of 0.51 as reported by the National Bureau of Standards (Velapoldi and Mienenz (1980) *Nat. Bur. Standards* Vol. 260–64). Thus, in a preferred embodiment, the relative quantum yield is thus the ratio of the integral of the emission scan of quinine sulfate ($Em_{std}=EM_{QS}$) divided by the absorbance (optical density) of the quinine sulfate at the excitation wavelength ($Abs_{std}$) to the integral of the sample emission scan ($Em_{Sample}$) divided by the absorbance (optical density) of the sample at the excitation wavelength. Relative quantum yield thus provides a measure of the efficiency of the fluorophore in converting absorbed light to emitted light. Methods of determining relative quantum yield are well known to those of skill in the art (see, e.g., Velapoldi and Mienenz, supra.) Fluorescence intensity is measured by any of a number of means well known to those of skill in the art. In a preferred embodiment, fluorescence intensity is determined in an aqueous solution using a fluorometer.

The term "oligonucleotide", as used herein, refers to a molecule comprised of two or more deoxyribonucleotides, ribonucleotides, modified ribonucleotides, modified dexoyribonucleotides, fluorescent or non-fluorescent ribonucleotide analogs, or fluorescent or non-fluorescent deoxyribonucleotide analogs. The exact size of an oligonucleotide depends on many factors and the ultimate function or use of the oligonucleotide. Generally, chemically synthesized oligonucleotides range is length from 2 to 200 bases, although, it is well known that oligonucleotides may be ligated together to provide longer sequences. As used herein, the term "oligonucleotide" also encompasses these longer sequences. It is also recognized that double-stranded polynucleotides may be created by hybridization with a complementary sequence or enzymatically through primer extension.

The term "label oligonucleotide", as used herein, refers to an oligonucleotide incorporating one or more fluorescent nucleotide analogues. The fluorescence activity of the nucleotide analogue(s) may be quenched partially or to a non-detectable level when the label oligonucleotide achieves a substantially linear conformation (i.e., the constituent bases, more particularly the fluorescent nucleotide(s), participate in normal base stacking). Preferred label oligonucleotides of this invention are capable of achieving a conformation, when hybridized to themselves or another nucleic acid or when bound by a nucleic acid binding protein, in which the quench (reduction of fluorescence activity (intensity) of the fluorescent nucleotide(s)) is diminished or eliminated resulting in a label oligonucleotide having increased fluorescence when present in that conformation. The label oligonucleotides of this invention are distinguished from labeled oligonucleotides which are oligonucleotides to which is attached a label. The labeled oligonucleotide can of course be attached to (labeled with) a label oligonucleotide of the present invention either directly through a phosphodiester linkage or indirectly through a linker.

"Subsequence" refers to a sequence of nucleic acids that comprise a part of a longer sequence of nucleic acids.

The terms "target nucleic acid" or "target oligonucleotide" refer to the nucleic acid sequence or nucleic acid subsequence that is to be detected using one or more label oligonucleotides of this invention. The label oligonucleotides typically hybridize to all or a part of the target nucleic acid under stringent conditions.

The term "corresponding nucleotide", is used to refer the position of a nucleotide in a first nucleic acid by reference to a second nucleic acid. Thus, a corresponding nucleotide refers to a nucleotide that would form a complementary base pair (i.e. would hydrogen bond) with the nucleotide in the first nucleic acid to which the correspondence is drawn, were the first and second nucleic acids perfectly complementary and hybridized under stringent conditions.

Hybridization refers to the specific binding of two nucleic acids through complementary base pairing. Hybridization typically involves the formation of hydrogen bonds between nucleotides in one nucleic acid and their corresponding nucleotides in the second nucleic acid.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule only to a particularly nucleotide sequence or subsequence under stringent conditions when that sequence is present in a complex mixture (e.g., total cellular DNA or RNA). The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. (As the target sequences are generally present in excess, at $T_m$, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

The term complementary base pair refers to a pair of bases (nucleotides) each in a separate nucleic acid in which each base of the pair is hydrogen bonded to the other. A "classical" (Watson-Crick) base pair always contains one purine and one pyrimidine; adenine pairs specifically with thymine (A-T), guanine with cytosine (G-C), uracil with adenine (U-A). The two bases in a classical base pair are said to be complementary to each other.

A "nucleic acid amplification mixture" refers to the reaction mixture used to amplify a nucleic acid. The amplification may be by any method including but not limited to PCR, long range PCR, ligase chain reaction, self-sustained sequence replication, and the like. Typical nucleic acid amplification mixtures (e.g., PCR reaction mixture) include a nucleic acid template that is to be amplified, a nucleic acid polymerase, nucleic acid primer sequence(s), and nucleotide triphosphates, and a buffer containing all of the ion species required for the amplification reaction.

BRIEF DESCRIPTION OF THE DRAWINGS

FIG. 2 shows the sequence of the nMyc gene (SEQ ID NO:16). Sites that are appropriate for insertion of the fluorophore are in bold. A restriction site map of the gene reveals sites which bracket the fluorophore insertion site resulting in a sequence of 20–38 bases for each site. For example, the sites for RD9 which is located between bases 896 and 922, are illustrated.

FIG. 3 provides the HXB2 restriction map showing sk38, sk39, and HIVPCR (SEQ ID NO:19) regions. Primers are underlined and bold, HIVPCR (SEQ ID NO:19) is bold only.

DETAILED DESCRIPTION

Figure 1:
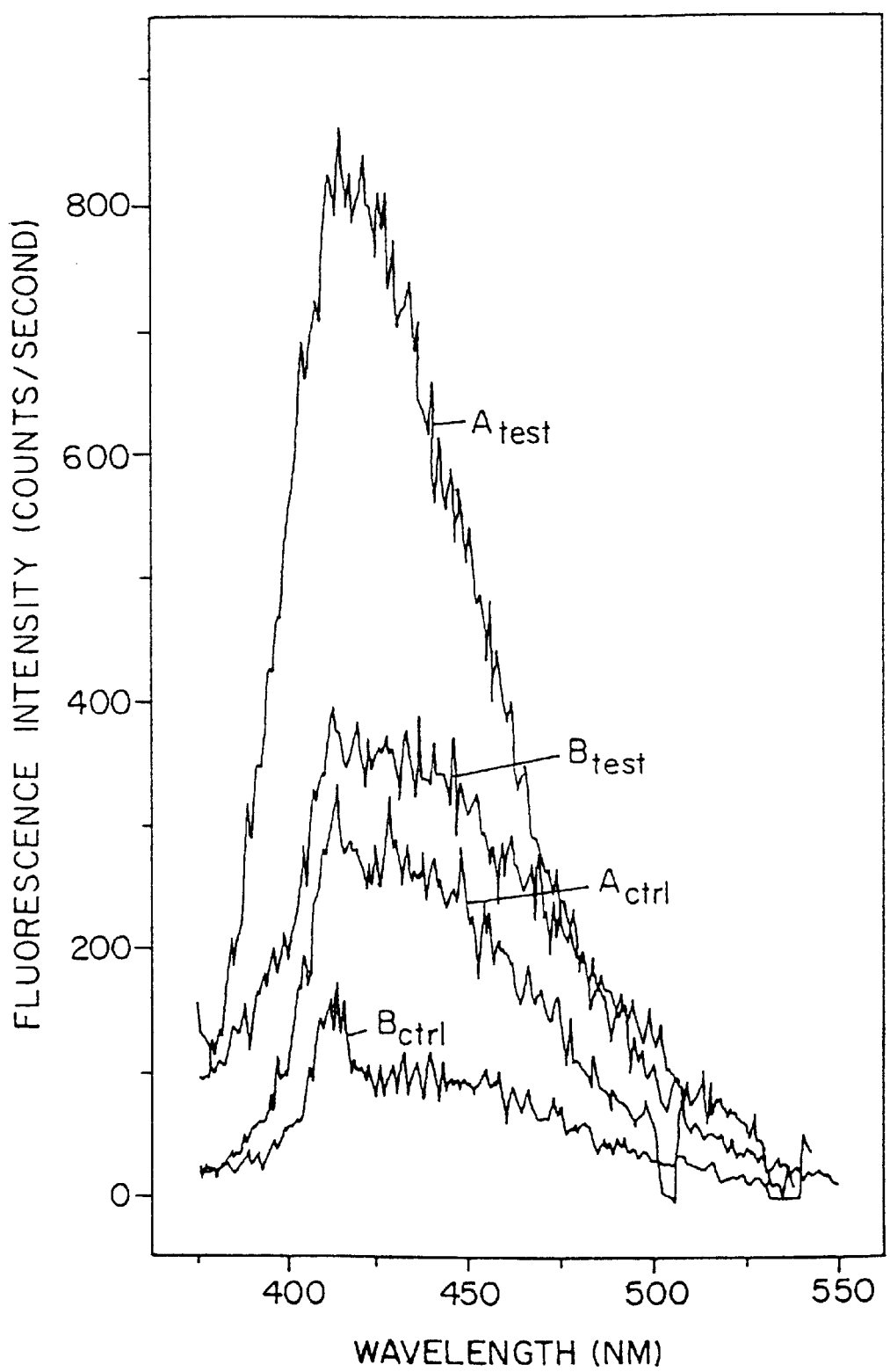
FIG. 1 illustrates the results of PCR amplification of a Pax3 template with a separate label oligonucleotide as described in Example 3. The graphs labeled $A_{test}$ and $B_{test}$ are amplified with PCR primers at 0.5 mM and at 0.2 mM respectively. The graphs labeled $A_{ctrl}$ and $B_{ctrl}$ are controls; the same reaction mixture absent thermocycling.

This invention provides new methods and compositions for the detection of nucleic acid interactions with other nucleic acids or with proteins. The methods and compositions utilize fluorescent nucleotide analogs as fluorescent moieties and thus are highly compatible with nucleic acid hybridization reactions and nucleic acid/protein interactions.

In particular, this invention is based, in part, on the surprising discovery that fluorescent nucleotide analogues whose fluorescence is quenched when they are incorporated into oligonucleotides can have some or all of the original fluorescence activity restored by disrupting (i.e., looping or folding produced by an insertion) the oligonucleotide. Without being bound to a particular theory, it is believed that quenching is mediated by interactions with adjacent nucleotides when the fluorescent nucleotide undergoes normal base stacking. Disruption of the normal base stacking of the fluorescent nucleotide, e.g, by kinking or folding the subject of oligonucleotide, diminishes or eliminates these interactions thereby restoring some or all of the fluorescence activity.

Oligonucleotides can be designed that contain fluorescent nucleotides in a conformation that does not permit normal base stacking. This can be a permanent feature of the oligonucleotide, such a hairpin produced by self-complementarity, in which case the fluorescent nucleotide in the hairpin will always fluoresce. Alternatively, the oligonucleotide can be designed so that normal base stacking is disrupted only when the oligonucleotide is hybridized to a target nucleic acid or bound by a nucleic acid binding protein. In this instance, the fluorescent oligonucleotide will fluoresce or increase fluorescence when the subject oligonucleotide hybridizes to its target. The molecule thus acts like a molecular beacon that only fluoresces when it is hybridized to a target. The oligonucleotides of this invention are thus "label oligonucleotides" that can act either as constant fluorescent labels or as molecular beacons that turn on to indicate molecular interactions.

I. Uses of Fluorescent Oligonucleotides

One of skill in the art will appreciate that the methods and molecules of this invention can be used in a wide variety of contexts. Three particularly preferred embodiments include the use of label oligonucleotides of this invention as "always fluorescent labels", the use of label oligonucleotides of this invention as "molecular beacons", and the use of label oligonucleotides of this invention as indicators in nucleic acid amplification reactions. These applications are discussed in detail below.

A) Always on Labels.

As indicated above, this invention is premised, in part, on the discovery that fluorescent nucleotide analogues whose fluorescence is quenched when they are incorporated into oligonucleotides can have some or all of the original fluorescence activity restored by disrupting (i.e., folding) the oligonucleotide. In one preferred embodiment, this invention provides oligonucleotides that are self complementary such that they form one or more hairpin loops through self-hybridization where each loop contains one or more fluorescent nucleotides in a conformation that prevents the fluorescent nucleotides from forming complementary base pairs. Under conditions that permit self-hybridization, normal base stacking of the fluorescent nucleotide is disrupted and the nucleotide fluoresces. These oligonucleotides thus continuously fluoresce and provide useful "always on" labels. Always on labels can also be produced by placing the fluorescent nucleotide at the 3' or 5' terminus, more preferably at the 5' terminus. In this position the fluorescent nucleotide, lacking a neighbor, is not as quenched as when it is located within the oligonucleotide. The "always on" fluorescence labels can be used in a manner analogous to fluorescent labels (e.g., fluorescein, rhodamine, etc.) known in the prior art.

Uses of such fluorescent labels are well known to those of skill in the art. They may be utilized for labeling virtually anything ranging from macroscopic objects to individual molecules. Thus, for example, various articles of manufacture (e.g., computer chips) can be labeled by attachment of the "always on" label oligonucleotides of this invention. The label will remain essentially undetected until the object is specifically examined for the presence of a fluorescent moiety, e.g., by illuminating the object with an appropriate excitation light source. Such labels provide a means of unobtrusively labeling objects to provide inventory tracking, an indication of ownership, and/or an indication of place of manufacture especially when such objects are misappropriated.

In a more preferred embodiment, the fluorescent oligonucleotides of this invention are used to label molecules, more preferably biological molecules such as other nucleic acids, proteins, and the like. Particularly preferred molecules to be labeled include antibodies, growth factors, cell-surface receptors, lectins, hormones, and the like. Indeed, the molecules that can be so labeled include virtually any molecules that can be linked to a nucleic acid. The oligonucleotides of this invention can be linked to the subject molecules e.g., proteins, or nucleic acids, directly, or through a linker.

Suitable linkers attaching nucleic acids to other molecules are well known to those of skill in the art. Generally linkers are either hetero- or homo-bifunctional molecules that contain two or more reactive sites that may each form a covalent bond with the nucleic acid and the molecule to which it is to be attached. For example, the label nucleic acids of this invention may be joined to the subject molecule by a peptide linker, by a straight or branched chain carbon chain linker, or by a heterocyclic carbon. The linkers may attach to convenient reactive moieties on the base (e.g., $NH_3$) to available hydroxyl groups on the ribose or to a terminal phosphate. Hetero-bifunctional cross linking reagents such as active esters of N-ethylmaleimide have been widely used (see, e.g., Lerner et al. (1981) *Proc. Nat. Acad. Sci. USA* 78: 3403–3407 and Kitagawa et al. (1976) *J. Biochem.,* 79: 233–236), and other suitable linkers are well known to those of skill in the art (see, e.g., Chapter 4 In *Monoclonal Antibodies, Principles and Applications,* Birch and Lennox, eds, Wiley-Liss, Inc. New York (1994)).

B) Molecular Beacons.

In a particularly preferred embodiment, the oligonucleotides of this invention have a nucleotide sequence that enables the molecules to act as molecular beacons. The term "molecular beacon", as used herein refers to a molecule capable of participating in a specific binding reaction and whose fluorescence activity changes when the molecule participates in that binding reaction.

Thus, for example, preferred molecular beacons of this invention are label oligonucleotides that show little or no fluorescence activity when the molecule is free in solution and yet show a detectable increase in fluorescence activity when bound to their target substrate. The molecules are designed so that interaction (e.g., binding) with the substrate (target) molecule introduces a change in conformation of the label oligonucleotide that results in a reduction of the quenching of the fluorescent nucleotide(s) present in the label oligonucleotide. Such changes in conformation preferably involve a disruption of the normal base stacking of the fluorescent nucleotide in the label oligonucleotide. Such disruptions are preferably produced by a one or more base pair mismatch between the label oligonucleotide and its target when the molecules are hybridized, by the formation of loops (e.g., hairpins) in the label oligonucleotide, by lack of complementarity between the fluorescent nucleotides and the corresponding nucleotides in the target, by folds introduced into the label oligonucleotides during protein binding interactions, and the like. The design of such label oligonucleotides is illustrated and explained below in Section II.

Particularly preferred molecular beacons have a relative quantum yield in the unbound (quenched) state that ranges from undetectable to about 0.8, more preferably from undetectable to about 0.1 M and most preferably from undetectable to about 0.05.

Virtually any detectable change in fluorescence on binding is useful. However, the larger the change in fluorescence, the easier it is to detect the binding event. Thus preferred molecular beacons show a 2-fold increase, more preferably at least a 5-fold increase and most preferably at least a 10-fold increase in fluorescence intensity on binding to the target molecule.

Because the molecular beacons of this invention provide little or no fluorescent signal in the unbound state, the unbound or non-specifically bound oligonucleotides contribute little or no fluorescence to a background signal. Use of the molecular beacons of this invention thus provides an improved signal to noise ratio in nucleic acid hybridizations as compared to the use of "always on" fluorescent labels. The fluorescent labels of this invention are thus particularly well suited for the detection of nucleic acid hybridization in a wide variety of contexts including, but not limited to, nucleic acid hybridization arrays, Southern blot hybridizations, in situ hybridization, and the like.

As indicated above, the label oligonucleotides can also be used to detect interactions with nucleic acid binding proteins (or other molecules). The fluorescent nucleotide analogue(s) present in the label oligonucleotide are located so that the normal planar base stacking is disrupted when the label oligonucleotide is bound by a protein (e.g., rec A protein, PI nuclease, HIV integrase, estrogen receptor, etc.). Again, the disruption reduces or eliminates the "quench" resulting in an increase in fluorescence activity of the protein/label oligonucleotide complex. The increased fluorescence can be easily detected as discussed below. The label oligonucleotide sequence is selected to that the label oligonucleotide is recognized and bound by the particular protein (or other molecule) of interest.

C) Nucleic Acid Amplification.

In another preferred embodiment, the label oligonucleotides of this invention provide a means of detecting the presence and/or absence and/or quantifying the product of a nucleic acid amplification reaction. In this embodiment, the nucleotide sequence of the label oligonucleotide is selected so that the base stacking of the fluorescent nucleotide(s) is not disrupted unless an amplification product is present.

In a preferred embodiment, the label oligonucleotide does not itself participate in the amplification reaction. It is simply present as a separate indicator molecule. In this context, the label oligonucleotide nucleotide sequence is selected so that a loop containing the fluorescent nucleotide (s) is formed when the label oligonucleotide hybridizes to the amplification product. An amplification product is formed, the label oligonucleotide hybridizes to that product, disrupting the base pair stacking and thereby increasing its fluorescence activity. As long as the label oligonucleotide is present in a molar excess (of the amplification product) the change in fluorescence intensity in the reaction vessel is proportional to the amount of amplification product. However, it is also desirable to maximize the signal to noise ratio. Therefore, in a preferred embodiment, the molar excess of label oligonucleotide is kept as low as possible to minimize generation of a background signal.

This approach eliminates the laborious and time consuming steps (e.g., gel electrophoresis of the reaction product) typically required to determine the presence or absence and/or quantify the reaction product. The amplification methods of this invention thus provide a rapid means of detecting or quantifying the results of an amplification-based assay.

The amplification methods of this invention are particularly well suited to use in diagnostic applications. Thus, for example, where it is desired to detect the presence, absence, or severity of a pathological state, or an infection by detecting a nucleic acid characteristic of the pathological state or infecting pathogen, the characteristic nucleic acid, or a subsequence thereof, is amplified from a biological sample using the amplification methods of this invention. The amplification mixture is then directly assayed for fluorescence providing a rapid and sensitive measure of the amount of amplification product. No electrophoretic gels or other separation and/or quantification methods are necessary. The method thus provides a rapid diagnostic assay. In addition, because these methods, utilize essentially a single step reaction in a nucleic acid amplification system they are also well suited to automated detection and/or quantification of reaction product.

Methods of performing nucleic acid amplification reactions are well known to those of skill in the art. For example, detailed protocols for performing polymerase chain reaction are found in *PCR Protocols, A Guide to Methods and Applications*, Innis et al., Academic Press, Inc. N.Y., (1990). Similarly, long range PCR (LR-PCR) is described by Barnes (1994) *Proc. Natl. Acad. Sci. USA*, 91:2216–2220 and Cheng et al. (1994) *Proc. Natl. Acad. Sci. USA*, 91:5695–5699. Other suitable amplification methods include, but are not limited to ligase chain reaction (LCR) (see Wu and Wallace (1989) *Genomics*, (1989) 4:560, Landegren, et al. (1988) *Science*, 241:1077, and Barringer, et al. (1990) *Gene*, 89:117, transcription amplification (Kwoh, et al. (1989) *Proc. Natl. Acad. Sci. USA*, 86:1173), and self-sustained sequence replication (Guatelli, et al. (1990) *Proc. Nat. Acad. Sci. USA*, 87:1874).

II. Nucleic Acid Sequence Selection.

As indicated above, the oligonucleotides of this invention contain one or more fluorescent nucleotide analogues. In addition, the nucleotide sequences of the oligonucleotides are selected such that the normal base stacking of the fluorescent nucleotide analogue and/or its adjacent nucleotides is disrupted either through self-hybridization of the oligonucleotide or when the oligonucleotide hybridizes to a target nucleic acid or when the oligonucleotide participates in a protein/DNA interaction. This is typically accomplished when the fluorescent nucleotide analogue(s) are located in loop(s).

The term nucleic acid loop, as used herein, refers to a region of one or more contiguous nucleic acids that do not participate in normal (e.g., purine/pyrimidine hydrogen bond formation) base pairing when the nucleic acid is hybridized to an otherwise complementary target nucleic acid. A loop also refers to a disruption of the normal planar base stacking of the nucleotide caused by binding of a nucleic acid binding protein (e.g., rec A protein, PI nuclease, HIV integrase, estrogen receptor, etc.).

In a preferred embodiment, the loops of this invention are formed as insertions in nucleic acid sequences. The insertion may comprise one or more nucleotides. As used herein an insertion refers to the addition of one or more nucleotides into an oligonucleotide that is otherwise complementary to a target nucleic acid or target nucleotide subsequence. The insertion is thus recognized by reference to the target nucleic acid sequence of subsequence. One of skill will appreciate that an insertion need not be produced by actual physical insertion of one or more additional nucleotides (bases) into an already existing oligonucleotide, but rather simply reflects the presence of the extra nucleotide(s) with reference to a particular target sequence or subsequence. Thus, the insertion-containing oligonucleotide can be synthesized de novo. Alternatively the insertion can be created by deleting one or more nucleotides in the target sequence or subsequence, or by synthesizing (e.g., polymerizing) a target sequence or subsequence lacking nucleotides corresponding to one or more nucleotides in the label oligonucleotide.

An example of an oligonucleotide of this invention with a one base insertion is shown in formula I, while a three base insertion is illustrated in Formula II:

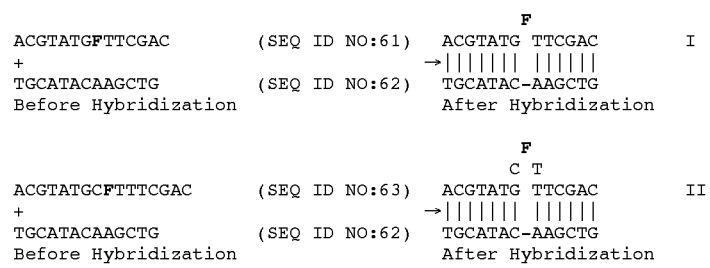

These formulas illustrate that annealing (hybridization) pushes the unmatched nucleotides out of the stacked conformation. This results in an increase in the fluorescent signal. As indicated above, the insertion can be as small as one base or virtually unlimited in length. There is essentially no limitation in the length of an insertion. In a preferred embodiment, however, the sequence of the insertion is selected such that when the label oligonucleotide is hybridized to it target, the base stacking of the fluorescent nucleotide(s) is disrupted thereby increasing the fluorescence intensity of the subject fluorescent nucleotide(s). Preferred insertions range in length from 1 nucleotide to about 100 nucleotides, more preferably from 1 to about 20 nucleotides, most preferably from 1 to about 10, 1 to about 5, or even 1 to about 3 nucleotides. In one particularly preferred embodiment, the insertion is a single nucleotide insertion comprising the fluorescent nucleotide analogue.

The loop-forming insertions can include nucleotides capable of forming complementary base pairs within the loop resulting in a hairpin conformation as illustrated in formula III.

```
        F
        C T
        T-A
        T-A
        C-G
```

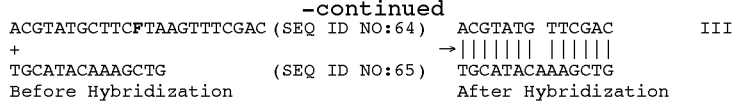

```
                                          -continued
ACGTATGCTTCFTAAGTTTCGAC (SEQ ID NO:64)    ACGTATG TTCGAC           III
+                                        →||||||| ||||||
TGCATACAAAGCTG          (SEQ ID NO:65)    TGCATACAAAGCTG
Before Hybridization                      After Hybridization
```

The hairpin conformation can be one that is stabilized by hybridization to the target nucleic acid as illustrated in Formula III, or it can be a stable formation in the label oligonucleotide even when the label oligonucleotide is not hybridized to the target substrate. In this case the base stacking of the label oligonucleotide is always disrupted resulting in a continually elevated fluorescence activity. The label oligonucleotide is an "always-on" label. Of course, the hairpin formation can be internal to the label oligonucleotide or alternatively can be formed at the terminus of the label oligonucleotide. Always on labels are illustrated in Formulas IV and V.

binding by a polypeptide. Similarly, where the nucleic acid is used as an amplification primer as described above, the sequence will be selected to provide appropriate priming in addition to the label functionality.

Methods of selecting and optimizing nucleic acid sequences for hybridization to particular targets and/or internal hybridization and/or priming of particular templates are well known to those of skill in the art (see, e.g., Innis et al. (1990) *PCR Protocols, A guide to Methods and Applications*, Innis et al., Academic Press, Inc. N.Y.). Such optimization is simplified by the use of nucleic acid sequence analysis software. Such software is well known to

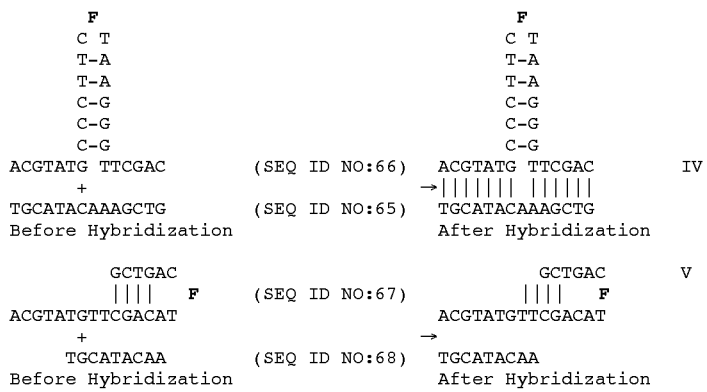

The label oligonucleotides of this invention can include one or more of the above-described loops. In addition, any loop can include one or more fluorescent nucleotide analogues. It was a discovery of this invention that the pteridine nucleotide analogues described below are particularly well quenched by adjacent nucleotides, in particular by adjacent purines. Thus in a particularly preferred embodiment the fluorescent nucleotide analogue(s) are located adjacent to one or more purines (e.g., adenosine or guanosine) more preferably the nucleotide analogue(s) are located between two adenosines, and most preferably the nucleotide analogue(s) are located with at least two adenosines on each side.

In still another embodiment, this invention provides method of nucleic acid amplification in which the detection of a nucleic acid amplification product is detected by formation of a loop in a label oligonucleotide of this invention. The label oligonucleotide can be provided as a separate label in the amplification reaction mixture and the label can include any of the above described oligonucleotide labels. The amplification product is then detected by hybridization with an always on label of this invention or by the formation of a loop in one of the molecular beacons of this invention.

The particular sequences of the label oligonucleotides will be selected to provide one or more of the above described loop formations when the label oligonucleotide is hybridized to the target nucleic acid, when the label oligonucleotide is bound in a nucleic acid/polypeptide interaction, or when the label oligonucleotide is or otherwise bound to a subject molecule. Where desired, the nucleic acid sequence is also selected to provide the requisite sequence for hybridization to a particular nucleic acid target or for recognition and those of skill in the art and includes, but is not limited to, HyperPCR, Loop Viewer, MulFold, Primer, and Amplify (available on the internet at PubNet), GeneWorks7, GeneJocky, DNA strider, LaserGene (DNAStar, Madison, Wis., USA), and the like.

The label oligonucleotides of this invention can be prepared by any of a wide variety of chemical and enzymatic methods. Chemical synthesis can be performed in solid phase or in solution. Generally, solid phase synthesis is preferred. Detailed descriptions of the procedures for solid phase synthesis of oligonucleotides by phosphite-triester, phosphotriester, and H-phosphonate chemistries are widely available (see, e.g., Itakura, U.S. Pat. No. 4,401,796; Caruthers et al., U.S. Pat. Nos. 4,458,066 and 4,500,707; Beaucage et al., (1981) *Tetrahedron Lett.*, 22:1859–1862; Matteucci et al. (1981) *J. Amer. Chem. Soc.*, 103:3185–3191; Caruthers et al. (1982) *Genetic Engineering*, 4:1–17; Jones, chapter 2, Atkinson et al., chapter 3, and Sproat et al., chapter 4, in Gait, ed. *Oligonucleotide Synthesis: A Practical Approach*, IRL Press, Washington D.C. (1984); Froehler et al. (1986) *Tetrahedron Lett.*, 27:469–472; Froehler et al. (1986) *Nucleic Acids Res.*, 14:5399–5407; Sinha et al. (1983) *Tetrahedron Lett.*, 245:5843–5846; and Sinha et al. (1984) *Nucl. Acids Res.*, 12:4539–4557).

One of skill in the art will appreciate that incorporation of the fluorescent nucleotide analogues into an oligonucleotide during chemical synthesis is preferably accomplished by derivatizing the fluorescent nucleotide as a protected nucleotide monomer reagent (e.g., as a phorphoramidite) compatible with the particular synthesis chemistry used to produce the oligonucleotide. Means of so derivatizing nucleotide analogues are well known to those of skill in the art. Typically this involves blocking the exocyclic amines and/or other reactive groups purine or pyrimidine analogue, derivatizing the phosphite moiety on the ribose with a reactive group appropriate to the particular synthetic chemistry contemplated, and blocking the 5' hydroxyl with a protecting group that may be removed during synthesis to facilitate the stepwise coupling of derivatized nucleotides to the 5' terminus of the growing oligonucleotide. Where the sugar of the nucleotide analogue is a ribose, the reactive 2'-hydroxyl group should must also be protected. The selection of protecting groups is well known to those of skill in the art. See, for example Greene et al. (1991) *Protective Groups in Organic Synthesis*, 2nd ed., John Wiley & sons, Inc. Somerset, N.J.

In particular, the derivitization of particular pteridines and lumazines as phosphoramidites and their incorporation into oligonucleotides using solid-phase phosphotriester chemistry is described in detail in U.S. Pat. No. .5,525,711 (see also Bannwarth et al., *Helvetica Chimica Acta*.(1991) 74:1991–1999, Bannwarth et al. (1991), *Helvetica Chimica Acta*. 74:2000–2007, and Bannwarth et al., European Patent Application No. 0439036A2). The derivitization of pteridines as nucleotide triphosphates is also described in U.S. Pat. No. 5,525,711.

Alternatively the label oligonucleotides of this invention can be prepared using enzymatic methods. This typically involves providing a template having a nucleotide sequence complementary to that of the desired label oligonucleotide. The label oligonucleotide is then produced by primer extension through polymerization of nucleotide triphosphate in solution using a nucleic acid polymerase (e.g., DNA or RNA polymerase). In this instance, the fluorescent oligonucleotide analogues are provided as nucleotide triphosphate for incorporation by the polymerase. Methods of enzymatically synthesizing nucleic acids are well known to those of skill in the art (see, e.g., Henderson et al. (1973) *Nucleotide Metabolism*, Academic Press, New York, Davidson (1972) *The Biochesmistry of Nucleic Acids*, Academic Press, New York, pp. 215–232).

III. Hybridization with Label Oligonucleotides.

As explained above, the label oligonucleotides of this invention can be used as "always on" labels and simply attached to the molecule or article of interest just like any other fluorescent marker. Alternatively, the label oligonucleotides are used as molecular beacons whose fluorescence activity increases when the molecules hybridize to a target nucleic acid or nucleic acid subsequence or when the label oligonucleotides are bound by a target protein.

The nucleic acid hybridization simply involves providing a denatured label oligonucleotide probe and target nucleic acid under conditions where the probe and its target can form stable hybrid duplexes through complementary base pairing. As described above, the label oligonucleotides have nucleic acid sequences that introduce a change in conformation on hybridizing that increases the fluorescence activity of the fluorescent nucleotide(s) present in the label oligonucleotide. The resulting fluorescent hybrid duplexes are then detected, e.g., using a spectrofluorometer.

It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency (e.g., about 20° C. to about 50° C., more preferably about 30° C. to about 40° C., and most preferably about 37° C. and 6X SSPE-T or lower for an oligonucleotide) to ensure hybridization and then subsequent washes are performed at higher stringency (e.g., typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotides) and at least about 50° C. or 60° C. for longer probes). Successive hybridizations may be performed at increasingly higher stringency (e.g., down to as low as 0.25×SSPE–T at 37° C. to 50° C.) until a desired level of hybridization specificity is obtained. Stringency can also be increased by addition of agents such as formamide.

Hybridization specificity may be evaluated by specific labeling of nucleic acids separated in gel electrophoresis, and/or by evaluation of the signal to noise (background fluorescence), or by other methods well known to those of skill in the art.

In general, there is a tradeoff between hybridization specificity (stringency) and signal intensity. Thus, in a preferred embodiment, the wash is performed at the highest stringency that produces consistent results and that provides a hybridization showing a readily detectable change in signal intensity (e.g., an increase in signal intensity of at least 20%, more preferably an increase in signal intensity of at least 50% and most preferably an increase in signal intensity of at least 100% (a doubling of signal intensity) over the background signal intensity.

The background signal can also be reduced by the use of a detergent (e.g., C-TAB) or a blocking reagent (e.g., sperm DNA, cot-1 DNA, etc.) during the hybridization to reduce non-specific binding. The use of blocking agents in hybridization is well known to those of skill in the art (see, e.g., Chapter 8 in *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993)).

The stability of duplexes formed between RNAs or DNAs are generally in the order of RNA:RNA>RNA:DNA>DNA:DNA, in solution. Long probes have better duplex stability with a target, but poorer discrimination than shorter probes, Shorter probes (e.g., 8-mers) are highly specific (discriminate mismatches very well), but the overall duplex stability is low. Methods of optimizing hybridization conditions are well known to those of skill in the art (see, e.g., *Laboratory Techniques in Biochemistry and Molecular Biology*, Vol. 24: *Hybridization With Nucleic Acid Probes*, P. T'ijssen, ed. Elsevier, N.Y., (1993)).

IV. Signal Detection.

Means of detecting the fluorescence signals produced by the label oligonucleotides of this invention are well known to those of skill in the art. Labeled target (sample) nucleic acids hybridized to the probes of the high density array are known to those of skill in the art. Typically detection is the same as that for any other fluorescent label. Such detection involves exposing the fluorescent moiety (i.e., the label oligonucleotide to an excitation illumination at the absorption wavelength of the fluorescent nucleotide analogue. The light is absorbed and re-emitted at the emission wavelength of the fluorescent nucleotide. Devices for detecting fluorescent labels are commercially available and include, but are not limited to, fluorometers, fluorescence microscopes, flow cytometers, fluorescence plate readers, and the like (see, e.g., Applied Imaging Corp, Santa Clara, Calif., USA; Perkin-Elmer Corp., Norwalk, Conn., USA; and Photon Technology International, South Brunswick, N.J., USA).

In a particularly preferred embodiment, fluorescence is detected using a PTI (Photon Technologies, Inc., New Brunswick, N.J., USA) spectrofluorometer with a double excitation monochromater, a water cooled photomultiplier, and a sample chamber coupled with a water bath (Pharmacia LKB, Piscataway, N.J., USA). Low volume measurements can be made using an "H" style cuvette with excitation over the long (e.g., 1 cm) path and emission through the short (e.g., 2 mm path). In another embodiment, 3 mm×3 mm square cuvettes with a brass adaptor have been successfully used. Measurements using systems like these are illustrated in Example 1.

In another embodiment the fluorescence of the label oligonucleotide can be detected indirectly through energy transfer through a second and even a third fluorophore. In this embodiment, a second fluorophore is provided that has an absorption wavelength at or about the emission wavelength of the fluorescent nucleotide analogue. When a fluorescent nucleotide analogue is excited, the energy it releases is absorbed (e.g., through resonance energy transfer) by the second fluorophore which then fluoresces at its characteristic wavelength. This approach is particularly convenient where it is desired to shift the signal to a wavelength different than the characteristic fluorescence wavelength of the fluorescent nucleotide. Resonance energy transfer system are well known to those of skill in the art (see, e.g., Forster (1948) *Ann. Phys.*, 2:55; Stryer et al. (1967) *Proc. Natl. Acad. Sci. USA*, 58:719–726, and Stryler (1978) *Ann. Rev. Biochem.*, 47:819).

V. Enhancement of Signal Detection.

In the label oligonucleotides of this invention, fluorophore containing nucleic acids bind with a (substantially) complementary target that does not contain a base-pairing partner for the fluorophore. As the label oligonucleotide probe hybridizes to its target, the fluorophore is squeezed out of the base stacking interactions responsible for quenching the fluorophore. This results in a substantial increase in fluorescence signal (e.g., up to 14 fold), the precise magnitude of which is dependent on the surrounding sequence.

However, where the label oligonucleotide probe is used in a mixture containing longer competing sequences, signal intensity is often diminished. Without being bound to a particular theory, it is believed this diminution in signal is a consequence of hybridization kinetics. One problem with using short probes to bind to large (e.g., genomic sized) nucleic acids is that at hybridization temperatures characteristic for oligonucleotides, larger nucleic acids are highly favored in binding and outcompete the label probes for hybridization to the target nucleic acid. The shorter label oligonucleotides therefore remain in solution and self-quench thereby reducing or eliminating the signal.

However, it was a discovery of this invention that this effect can be offset and significant signal restored by shifting the binding equilibrium in favor of the label oligonucleotides. This can be accomplished by providing a significant excess of label oligonucleotide.

In addition or alternatively, and in a preferred embodiment, the binding equilibrium can also be shifted by reducing the average size of the target nucleic acids in the mixture until they more closely approximate the size of the label oligonucleotide. This is most simply accomplished by fragmenting the nucleic acids (e.g., by sonication, extrusion through a porous membrane, acid treatment, or by the use of restriction endonucleases). In a preferred embodiment the nucleic acids are digested by restriction endonucleases. Restriction sites are quite abundant throughout most gene sequences and the average fragment length produced can be regulated by the size of the restriction site for which a particular restriction endonuclease is specific. The longer the restriction site, typically the less frequently the site will occur in a sample and the longer the average fragment length produced by digestion. It will be appreciated that shorter fragments can be prepared by the use of several different restriction endonucleases.

Means of selecting an endonuclease to provide a characteristic fragment length are well known to those of skill in the art (see, e.g., Ausubel et al. (1997) *Current Protocols In Molecular Biology*, Vol. 1 Wiley, N.Y.).

Where the nucleic acid it is desired to detect (target nucleic acid) is amplified, (e.g., from a genomic DNA sample, from a polyA mRNA sample, etc.) it is preferable to digest the nucleic acids after amplification in order to avoid destruction of the template and/or the restriction endonuclease. However, it will be appreciated that the target (template) can be selected such that it lacks the restriction sites that permit digestion in which case it may be possible to digest the sample prior to amplification. In this instance, where the restriction endonuclease(s) are tolerant of the amplification conditions it may be possible to perform the digestion simultaneous with the amplification protocol.

It will also be appreciated that rather than decreasing the size of the other nucleic acids in the mixture, longer label oligonucleotides can be used Moreover, it is expected that particular target sequences will be detectable in a genomic DNA sample without any amplification of the target sequence.

The use of restriction digest to enhance label oligonucleotide signal is illustrated in Example 5.

VI. Fluorescent Nucleotide Analogues

A large number of fluorescent nucleotide analogues are suitable for use in the methods and compositions of this invention. Fluorescent nucleotide analogues are well known to those of skill in the art. Fluorescent nucleotide analogues include, but are not limited to 2'-deoxyisoinosine (Seela et al. (1995) *Nucleosides Nucleotides*, 14:863–866), formycin, 2-amino purine, 2,6-diaminopurine, and their derivatives (Ward et al. (1969) *J. Biol. Chem.*, 244:1228–1237), 8-amino-9, 10-dihydro-10-oxo-3-β-D -ribofuranosyl-3H-1, 3,5-triazino[1,2-a]purine, 1A'-metamorphosine (Leonard et al. (1984) *J. Am. Chem. Soc.*, 106:6847–6848), 2-pyrimidinone-1-β-D-riboside (Adams et al. (1994) *Tet. Letts.*, 35:1597–1600), fluorescent N-nucleosides and analogues (WO 9316094), 3,6-dioxopyrimido(4,5-d) isoquinoline (JP 62059293, JP 91071437), etheno-substituted nucleotides (Leonard (1994) *CRC Crit. Rev. Biochem.*, 15(2): 125–199, and the like.

In a particularly preferred embodiment, the fluorescent nucleotide analogues are those described in U.S. Pat. No. 5,525,711. As unprotected nucleotide monomers these fluorescent nucleotide analogues are pteridine nucleotides of Formula VIII.

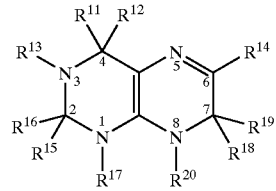

(VIII)

These nucleotide monomers are pteridine derivatives with ring vertices 1 through 8 as shown, where $R^{11}$ is combined with $R^{12}$ to form a single oxo oxygen joined by a double bond to ring vertex 4, or with $R^{13}$ to form a double bond between ring vertices 3 and 4; $R^{12}$, when not combined with $R^{11}$, is $NH_2$; $R^{13}$ when not combined with $R^{11}$ is a lower alkyl or H; $R^{14}$ is either H, lower alkyl or phenyl; $R^{15}$ is combined with $R^{16}$ to form a single oxo oxygen joined by a double bond to ring vertex 2, or with $R^{17}$ to form a double bond between ring vertices 1 and 2, such that ring vertices 2 and 4 collectively bear at most one oxo oxygen; and $R^{16}$ when not combined with $R^{15}$ is H, phenyl, or $NH_2$. When $R^{15}$ is not combined with $R^{16}$, $R^{18}$ is combined with $R^{19}$ to form a single oxo oxygen joined by a double bond to ring vertex 7. When $R^{15}$ is combined with $R^{16}$, $R^{18}$ is combined with $R^{20}$ to form a double bond between ring vertices 7 and 8, and $R^{19}$ is either H or a lower alkyl. $R^{17}$ when not combined with $R^{15}$, or $R^{20}$ when not combined with $R^{18}$, are a ribose or a deoxyribose having a phosphate attached through the 3' hydroxyl. In a preferred embodiment $R^{14}$ is hydrogen, a methyl or a phenyl, more particularly a hydrogen or a methyl.

In another preferred embodiment, $R^{16}$, when not combined with $R^{15}$, is a hydrogen, a phenyl, or amino group. More preferably particularly, $R^{16}$ is a hydrogen or a phenyl.

In yet another preferred embodiment when $R^{18}$ is combined with $R^{20}$, $R^{19}$ is a hydrogen or a methyl.

In still yet another preferred embodiment, $R^{14}$ is a hydrogen, a methyl, or a phenyl, $R^{16}$, when not combined with $R^{15}$, is a hydrogen, a phenyl or an amino, and, when $R^{18}$ is combined with $R^{20}$, $R^{19}$ is a hydrogen or a methyl.

Among the pteridine nucleotides used in the present invention, nine embodiments are particularly preferred. In a first preferred embodiment $R^{11}$ is combined with $R^{13}$ to form a double bond between ring vertices 3 and 4, $R^{12}$ is $NH_2$; $R^{14}$ is H; $R^{15}$ is combined with $R^{17}$ to form a double bond between ring vertices 1 and 2, $R^{16}$ is a phenyl; $R^{18}$ is combined with $R^{19}$ to form a single oxo oxygen joined by a double bond to ring vertex 7; and $R^{20}$ is a ribose or deoxyribose bearing a 3' phosphate. This embodiment, designated 4-amino-2-phenyl-8-(2-deoxy-β-D-ribofuranosyl)pteridine-7-one or 4-amino-2-phenyl-8-(β-D-ribofuranosyl)pteridine-7-one, is illustrated by formula IX.

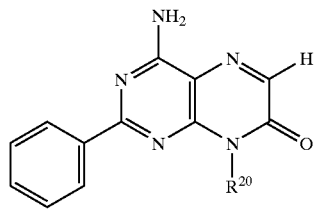

(IX)

In a second preferred embodiment $R^{11}$ is combined with $R^{13}$ to form a double bond between ring vertices 3 and 4, $R^{12}$ is $NH_2$; $R^{14}$ is a phenyl; $R^{15}$ is combined with $R^{17}$ to form a double bond between ring vertices 1 and 2; $R^{16}$ is a hydrogen; $R^{18}$ is combined with $R^{19}$ to form a single oxo oxygen joined by a double bond to ring vertex 7 and $R^{20}$ is a ribose or a deoxyribose bearing a 3' phosphate. This embodiment, designated 4-amino-6-phenyl-8-(2-deoxy-β-D-ribofuranosyl)pteridine-7-one or 4-amino-6-phenyl-8-(β-D-ribofuranosyl)-pteridine-7-one, where $R^{20}$ is a deoxyribose or a ribose respectively, is illustrated by Formula X.

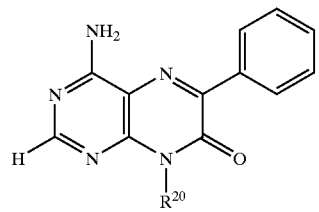

(X)

In a third preferred embodiment $R^{11}$ is combined with $R^{12}$ to form a single oxo oxygen joined by a double bond to ring vertex 4; $R^{13}$ is $CH_3$, $R^{14}$ is H; $R^{15}$ is combined with $R^{17}$ to form a double bond between ring vertices 1 and 2; $R^{16}$ is $NH_2$; $R^{18}$ is combined with $R^{19}$ to form a single oxo oxygen joined by a double bond to ring vertex 7; and $R^{20}$ is a ribose or deoxyribose bearing a phosphate attached through the 3' hydroxyl. This molecule, designated 3-methyl-8-(2-deoxy-β-D-ribofuranosyl) isoxanthopterin or 3-methyl-8-(β-D-ribofuranosyl) isoxanthopterin, where $R^{20}$ is a deoxyribose or a ribose respectively, is illustrated by Formula XI.

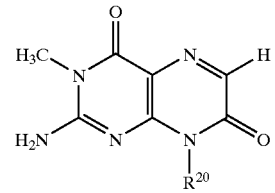

(XI)

In a fourth preferred embodiment $R^{11}$ is combined with $R^{12}$ to form a single oxo oxygen joined by a double bond to ring vertex 4; $R^{13}$ is a hydrogen; $R^{14}$ is hydrogen; $R^{15}$ is combined with $R^{17}$ to form a double bond between ring vertices 1 and 2; $R^{16}$ is $NH_2$; $R^{18}$ is combined with $R^{19}$ to form a single oxo oxygen joined by a double bond to ring vertex 7; and $R^{20}$ is a ribose or deoxyribose bearing a phosphate attached through the 3' hydroxyl. This embodiment, designated 2'-deoxy-β-D-ribofuranosyl-isoxanthopterin or β-D-ribofuranosyl-isoxanthopterin, where $R^{20}$ is a deoxyribose or a ribose respectively, is illustrated by formula XII.

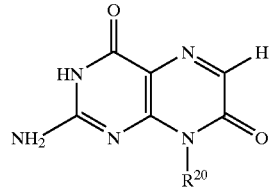

(XII)

In a fifth preferred embodiment $R^{11}$ is combined with $R^{12}$ to form a single oxo oxygen joined by a double bond to ring vertex 4; $R^{13}$ is a hydrogen; $R^{14}$ is $CH_3$; $R^{15}$ is combined with $R^{17}$ to form a double bond between ring vertices 1 and 2; $R^{16}$ is $NH_2$; $R^{18}$ is combined with $R^{19}$ to form a single oxo oxygen joined by a double bond to ring vertex 7; and $R^{20}$ is a ribose or deoxyribose bearing a phosphate attached through the 3' hydroxyl. This embodiment, designated or 6-methyl-8-(β-D-ribofuranosyl)isoxanthopterin or 6-methyl-8-(2-deoxy-β-D-ribofuranosyl) isoxanthopterin, where $R^{20}$ is a ribose or a deoxyribose respectively, is illustrated by formula XIII.

(XIII)

In a sixth preferred embodiment $R^{11}$ is combined with $R^{13}$ to form a double bond between ring vertices 3 and 4; $R^{12}$ is $NH_2$; $R^{14}$ is $CH_3$; $R^{15}$ is combined with $R^{16}$ to form a single oxo oxygen joined by a double bond to ring vertex 2; $R^{17}$ is a ribose or deoxyribose bearing a phosphate attached through the 3' hydroxyl; $R^{18}$ is combined with $R^{20}$ to form a double bond between ring vertices 7 and 8; and $R^{19}$ is $CH_3$. This embodiment, designated 4-amino-6,7-dimethyl-1-(2-deoxy-β-D-ribofuranosyl)-pteridine-2-one or 4-amino-6,7-dimethyl-1-(β-D-ribofuranosyl)-pteridine-2-one, where $R^{20}$ is a deoxyribose or a ribose respectively, is illustrated by formula XIV.

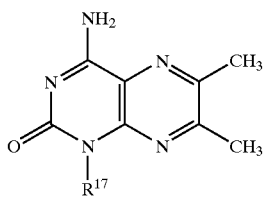

(XIV)

In a seventh preferred embodiment $R^{11}$ is combined with $R^{13}$ to form a double bond between ring vertices 3 and 4; $R^{12}$ is $NH_2$; $R^{14}$ is H; $R^{15}$ is combined with $R^{16}$ to form a single oxo oxygen joined by a double bond to ring vertex 2; $R^{17}$ is a ribose or deoxyribose bearing a phosphate attached through the 3' hydroxyl; $R^{18}$ is combined with $R^{20}$ to form a double bond between ring vertices 7 and 8; and $R^{19}$ is $CH_3$. This embodiment, designated 4-amino-1-(2-deoxy-β-D-ribofuranosyl)-7-methyl-pteridine-2-one or 4-amino-1-(β-D-ribofuranosyl)-7-methyl-pteridine-2-one, where $R^{17}$ is a deoxyribose or a ribose respectively, is illustrated by formula XV.

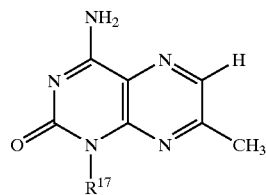

(XV)

In an eighth preferred embodiment $R^{11}$ is combined with $R^{13}$ to form a double bond between ring vertices 3 and 4; $R^{12}$ is $NH_2$; $R^{14}$ is $CH_3$; $R^{15}$ is combined with $R^{16}$ to form a single oxo oxygen joined by a double bond to ring vertex 2; $R^{17}$ is a ribose or deoxyribose bearing a phosphate attached through the 3' hydroxyl; $R^{18}$ is combined with $R^{20}$ to form a double bond between ring vertices 7 and 8; and $R^{19}$ is H. This embodiment, designated 4-amino-1-(2-deoxy-β-D-riobfuranosyl)-6-methyl-pteridine-2-one or 4-amino-1-(β-D-riobfuranosyl)-6-methyl-pteridine-2-one, where $R^{17}$ is a deoxyribose or a ribose respectively, is illustrated by formula XVI.

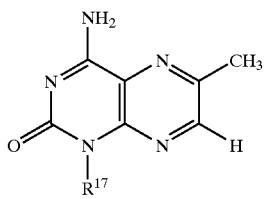

(XVI)

In a ninth preferred embodiment $R^{11}$ is combined with $R^{13}$ to form a double bond between ring vertices 3 and 4; $R^{12}$ is $NH_2$; $R^{14}$ is H; $R^{15}$ is combined with $R^{16}$ to form a single oxo oxygen joined by a double bond to ring vertex 2; $R^{17}$ is a ribose or deoxyribose bearing a phosphate attached through the 3' hydroxyl; $R^{18}$ is combined with $R^{20}$ to form a double bond between ring vertices 7 and 8; and $R^{19}$ is H. This embodiment, designated 2-amino-1-(2-deoxy-β-D-ribofuranosyl)-pteridine-2-one or 2-amino-1-(β-D-ribofuranosyl)-pteridine-2-one, where $R^{17}$ is a deoxyribose or a ribose respectively, is illustrated by Formula XVII.

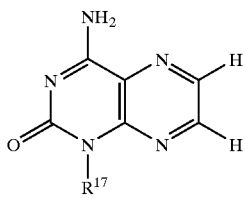

(XVII)

One of skill in the art will appreciate that other fluorescent nucleotide analogues can be used in the label oligonucleotides and in the methods of this invention. Such fluorescence nucleotide analogues can be identified by simple screening as described below in Section IV.

VII. Screening for Additional Fluorescent Nucleotide Analogues

Identification of additional fluorescent nucleotides suitable for practice of this invention can be accomplished with simple, rapid, and routine screening. The fluorescent nucleotide in question is simply incorporated into an oligonucleotide such that, when the oligonucleotide is hybridized to a target nucleic acid, the fluorescent nucleotide is present in a loop as described above. Most preferably the "test" label oligonucleotide is designed so the fluorescent nucleotide(s) are present as single base insertion(s). The fluorescence of the oligonucleotide is then determined. Then the oligonucleotide is hyridized to a target nucleic acid to form a hybrid duplex and the fluorescence level of the hybrid duplex is determined. Those fluorescent nucleotide analogues that show an increase in fluorescence when the test label oligonucleotide is hybridized to its target are suitable for use in the methods of this invention. Examples of such an assay are provided in Example 1.

The fluorescent nucleotide analogue can optionally be pre-screened by determining the fluorescence of the fluorescent nucleotide analogue monomer and then determining the fluorescence of the oligonucleotide incorporating the fluorescent nucleotide monomer(s). Those fluorescent nucleotide analogues that show a decrease in fluorescence when they are incorporated into an oligonucleotide are good candidates for further screening as described above.

One of skill in the art will appreciate that the label oligonucleotides of this invention can be optimized for particular applications. Such optimization can include varying the number of fluorescent nucleotide analogues in the label oligonucleotide, varying the number, size, and type of loop-forming regions, and varying the selection of nucleotides bracketing the fluorescent nucleotide analogues. Determination of the optimal label oligonucleotide base sequence simply involves preparing the variants in question and screening them for changes in fluorescence activity on hybridization to a target nucleic acid as described above (e.g., using a spectrofluorometer). Those label oligonucleotides showing the greatest change in fluorescence on hybridization are generally preferred.

Where the label oligonucleotide is to be used in conjunction with a nucleic acid binding protein, the binding protein is substituted for the target nucleic acid in the assays described above. The assay conditions are changed from hybridization conditions to conditions that favor binding of the particular nucleic acid binding protein to a nucleic acid. Those label nucleic acids that show an increase in fluorescence upon protein binding are suitable for use in the methods of this invention. One protein binding assay is illustrated by Example 4.

Identification of fluorescent nucleotide analogues that can be read through by a nucleic acid polymerase can also be readily accomplished with only routine screening. This simply involves providing a template nucleic acid incorporating the fluorescent nucleotide analogue in question, performing a polymerization reaction (e.g., as described by Berger and Kimmel, *Guide to Molecular Cloning Techniques, Methods in Enzymology* 152 Academic Press, Inc., San Diego, Calif.; Sambrook et al. (1989) *Molecular Cloning—A Laboratory Manual* (2nd ed.) Vol. 1–3, Cold Spring Harbor Laboratory, Cold Spring Harbor Press, N.Y.; *Current Protocols in Molecular Biology*, F. M. Ausubel et al., eds., Current Protocols, a joint venture between Greene Publishing Associates, Inc. and John Wiley & Sons, Inc., (1994 Supplement), Cashion et al., U.S. Pat. No. 5,017,478; and Carr, European Patent No. 0,246,864), and comparing the length of the polymerized product with the template (e.g., via gel electrophoresis). In one preferred embodiment, this polymerization can be accomplished in a nucleic acid amplification reaction (e.g., PCR). In a particularly preferred embodiment, where the fluorescent nucleotide analogue is known to function in a label oligonucleotide of this invention, a PCR reaction such as that described in Example 3, can be used to rapidly determine if the polymerase reads through the fluorescent nucleotide analogue.

VIII. Kits

An additional aspect of the invention relates to kits useful for the detection of nucleic acid/nucleic acid interactions and/or for the detection of protein/nucleic acid interactions and/or for the detection of amplification product. These kits take a variety of forms and can comprise one or more containers containing one or more label oligonucleotides of this invention. The label oligonucleotides can be "always on" probes or "molecular beacons" as described above. The label oligonucleotides can be simple "indicators" of a particular nucleic acid or protein target, or they can be amplification primers for amplification and detection of a particular target nucleic acid. Other optional components of the kit include, for example, a polymerase, a reaction-vessel, a second fluorophore for detection through resonance energy transfer, the appropriate buffers for PCR or other amplification reactions, positive and negative controls for diagnostic application, and the like. In addition to the above components, the kit can also contain instructions for carrying out the described method.

EXAMPLES

The following examples are offered to illustrate, but not to limit the claimed invention.

Example 1
Fluorescence Measurements of Label Oligonucleotides

Oligonucleotides were prepared and purified as described previously (Hawkins et al. (1996) *Nucleic Acids Res.,* 23: 2872–2880). Various label oligonucleotides were synthesized containing the fluorophore (3-methyl-8-(2-deoxy-β-D-ribofuranosyl) isoxanthopterin (surrounded by different bases, some with one fluorophore and others with multiple fluorescent nucleotides per strand.

Fluorescence measurement were done on a PTI (Photon Technologies, Inc., New Brunswick, N.J., USA) spectrofluorometer with a double excitation monochromater, a water cooled photomultiplier, and a sample chamber coupled with a water bath (Pharmacia LKB, Piscataway, N.J., USA). Excitation at 360 nm resulted in an emission at 440 nm. To reduce the volume of sample needed, "H" style cuvettes (100 ml minimum volume) were used with excitation over the 1 cm path and emission through the 2 mm path. Alternatively, 3 mm×3 mm cuvettes fitted with brass adaptors were used (60 ml minimum volume). In each case a fluorescence emission scan of the single strand was measured and then compared with the fluorescence emission scan of the same strand annealed to its complement. The integrals of the emission spectra were compared to determine the extent of increase in fluorescence signal.

In most cases, the fluorophore was forced to form a one base loop hairpin upon annealing. Two and three base loops were formed by omitting complementary bases of two or three bases (including the fluorescent nucleotide). In some instances, more than one fluorophore was placed in a strand.

Melting temperature of double-stranded oligonucleotides was measured by monitoring absorbance hyperchromicity at 260 nm in a spectrophotometer (Hewlett Packard Model 8452a equipped with a Hewlett Packard 89090A Peltier temperature controller). Samples were measured in 10 mM Tris, pH 7.5 with a NaCl concentration of 10 mM. Temperature was increased by 1° C. per minute with a 1 minute equilibration time between measurements.

Increase in fluorescence activity on hybridization with a target oligonucleotide is illustrated in Table 1.

TABLE 1

Increase in fluorescence intensity of label oligonucleotides where the fluorescent nucleotide is a single base insertion. The fluorescent nucleotide (F) was 3-methyl-8-(2-deoxy-β-D-ribofuranosyl) isoxanthopterin (Formula XI).

| ID | Sequence | Increase in fluorescence on hybridization | Seq. ID No. |
|---|---|---|---|
| PCR4 | 5'-att cca caa F gcc gtg tca-3' | ~6 fold | 1 |
| PCR5 | 5'-ggc tgg taa F gag tgc tcc-3' | ~9 fold | 2 |
| PCR6 | 5'-tct ctc gaa F agc ccg ctc-3' | ~8 fold | 3 |
| PCR7-1 | 5'-acc gct gaa F gag gaa gca-3' | ~4 fold | 4 |
| HP-3 | 5'-cct cta aga ggt gtg t F g gtg tgg aga atc tcc | ~2 fold | 5 |

In a second experiment, label oligonucleoties containing increasing numbers of fluorescent nucleotides were produced and evaluated as described above. The results are illustrated in Table 2.

TABLE 2

Change in fluorescence activity on hybridization of label of oligonucleotides containing varying numbers of fluorescent nucleotide analogues (Each F comprises a single base insertion).

| ID | Sequence | Increase in fluorescence on hybridization | Seq. ID No. |
|---|---|---|---|
| PCR2-1 | 5'-gca aga tgg agg aaa caa F ggc tgg agc caa-3' | ~8 fold | 6 |
| PCR2-2 | 5'-gca aga tgg agg F aaa caa F ggc tgg agc caa-3' | ~8 fold | 7 |
| PCR2-3 | 5'-gca a F ga tgg agg F aaa caa F ggc tgg agc caa-3' | ~10 fold | 8 |
| PCR2-4 | 5'-gca a F ga tgg agg F aaa caa F ggc tgg F agc caa-3' | ~10 fold | 9 |
| PCR2-1/3 | 5'-gca a F ga tgg agg aaa caa F ggc tgg agc caa-3' | ~7.5 fold | 10 |
| PCR3-1 | 5'-cgg cag agc tgg F agg aac tgg agc ggg-3' | no change | 11 |
| PCR3-2 | 5'-cgg cag F agc tgg F agg aac tgg agc ggg-3' | no change | 12 |

TABLE 2-continued

Change in fluorescence activity on hybridization of label of oligonucleotides containing varying numbers of fluorescent nucleotide analogues (Each F comprises a single base insertion).

| ID | Sequence | Increase in fluorescence on hybridization | Seq. ID No. |
|---|---|---|---|
| PCR3-3 | 5'-cgg cag F agc tgg F agg aac tgg F agc ggg-3' | no change | 13 |
| PCR7-1 | 5'-acc gct gaa F gag gaa gca-3' | ⁻4 fold | 14 |
| PCR7-2 | 5'-acc gct gaa F gag gaa F gca-3' | ⁻2 fold | 15 |

In another experiment, the effect of larger regions of mismatch and variations in the nucleotides neighboring the fluorescent nucleotide was investigated. The results are illustrated in Table 3.

TABLE 3

Effects of multiple base loops and various neighboring nucleotides on the change in fluorescence activity on hybridization of label oligonucleotides.

| ID | Sequence label oligonucleotide target oligonucleotide | Increase in fluorescence on hybridization | Seq. ID No. |
|---|---|---|---|
| HP3 | 5'-cct cta aga ggt gtg tFg gtg tgg aga atc tcc | ~2 fold | 17 |
| HP1C | 3'-gga gat tct cca cac c a cac acc tct tag agg | | 18 |
| HP3 | 5'-cct cta aga ggt gtg tFg gtg tgg aga atc tcc | no change | 17 |
| HP3C | 3'-gga gat tct caa cac cac acc tct tag agg | | 20 |
| HP2 | 5'-cct cta aga ggt gtg tF gtg tgg aga atc tcc | no change | 21 |
| HP3C | 3'-gga gat tct caa cac cac acc tct tag agg | | 20 |
| HPR | 5'-cct cta aga ggt gta cFa gtg tgg aga atc tcc | no change | 23 |
| HPRC | 3'-gga gat tct cca cat gt cac acc tct tag agg | | 24 |
| HP-4 | 5'-cct cta aga ggt gta aFa gtg tgg aga atc tcc | ~3 fold | 25 |
| HP-4C | 3'-gga gat tct cca cat t t cac acc tct tag agg | | 26 |
| HP5 | 5'-cct cta aga ggt gtc cFc ctg tgg aga atc tcc | ~2–3 fold | 27 |
| HP5C | 3'-gga gat tct cca cag g g gac acc tct tag agg | | 28 |
| PCR1 | 3'-ggc ttt cga gag Faa ccc act acc ca | ~5 fold | 29 |
| PCR1C | 3'-ccg aaa gct ctc tt ggg tga tgg gt | | 30 |
| HP6 | 5'-cct cta aga ggt gta aFa atg tgg aga atc tcc | ~10 fold | 31 |
| HP6C | 3'-gga tat tct cca cat t t tac acc tct tag agg | | 32 |

In these experiments, the best results were obtained with the sequences (GTAAFAATG) (from SEQ ID NO:31) or (GTAAFGAGT) (from SEQ ID NO:2)>(CGAAFAGCC) (from SEQ ID NO:3) or (ACAAFGGCT) (from SEQ ID NO:6)>(ACAAFGCCG) (from SEQ ID NO:1). It is believed that the nucleotide closest to the fluorescent nucleotide is most important with diminishing effect with increasing distance from the fluorescent nucleotide. The $T_m$s show only a one degree depression from the presence of a 1-base mismatch in a 21 mer. With multiple insertions per strand, this effect is more than additive. Two base or three base mismatches with one fluorescent nucleotide each did not display an increase in signal upon annealing, although it is expected that using other fluorescent nucleotides in the loop, or otherwise increasing the disruption of base stacking will produce a signal.

With respect to the one base insertion that did not show an increased fluorescence signal upon hybridization (HPR hybridized to HPRC) the sequence used in this signal oligonucleotide is one that is expected to show the least strained (disrupted base stacking) on hybridization based on computer modeling of hairpins. It is believed that the strain introduced by hybridization of the HPR label oligonucleotide was insufficient to cause a disruption of base stacking thereby accounting for the lack of a fluorescence signal increase on hybridization.

Example 2
Use of 2-Aminopurine Label Oligonucleotides

In another experiment, a number of label oligonucleotides of this invention were made incorporating 2-amino purine as the fluorescent nucleotide. The hybridizations and detection was performed as described above with the exception that excitation was at 317 nm and emission (detection) was collected from 322 to 400 nm. As illustrated in Table 4, the label oligonucleotides utilizing 2-amino purine generally gave good results.

TABLE 4

Changes in fluorescence on hybridization of 2 amino purine label oligonucleotides.

| ID | Sequence label oligonucleotide target oligonucleotide | Increase in fluorescence on hybridization | Seq. ID No. |
|---|---|---|---|
| PCR1ap | 5'-ggc ttt cga gag Faa ccc act acc ca-3' | ⁻5.6 fold | 33 |
| PCR2ap1 | 5'-gca aga tgg agg aaa caa F ggc tgg agc caa | ⁻2.5 fold | 34 |
| PCR2ap2 | 5'-gca aga F tgg agg aaa caa ggc tgg agc caa | ⁻2 fold | 35 |
| PCR3ap1 | 5'-cgg cag agc agc tgg agg F aac tgg agc ggg | ⁻1 fold | 36 |
| PCR3ap2 | 5'-cgg cag agc F agc tgg agg aac tgg agc ggg | no change | 37 |
| PCR4ap | 5'-att cca caa F gcc gtg tca | ⁻3 fold | 38 |
| PCR5ap | 5'-ggc tgg taa F gag tgc tcc | ⁻2 fold | 39 |
| PCR6ap | 5'-tct ctc gaa F agc ccg ctc | ⁻2 fold | 40 |
| PCR7ap1 | 5'-acc gct gaa F gag gaa gca | ⁻10 fold | 41 |

Example 3
PCR Amplification Using a Separate Label Oligonucleotide as a Detection Moiety Polymerase chain reaction (PCR) was performed to amplify a template which is part of the message of Pax3, a developmental gene (see Table 5). Total RNA from tumor cells was reverse transcribed using the Gene Amp RNA PCR kit (Perkin Elmer, Cetus, Foster City, Calif., USA). The cDNA thus produced was used as a template for the PCR amplification. PCR amplifications were performed for 35 cycles at 94° C. for 1 minute, 55° C. for 1 minute, and 72° C. for 1.5 minutes followed by a final extension at 72° C. for 10 minutes using primers PCR1 (5'-ACCTCAGTCAGATGAAGGCTCCGAT-3' (SEQ ID NO:42) see PCR1 in Table 5) and PCR2 (5'-AGTAGCACCGTCCACAGACCCTCAG-3' (SEQ ID NO:43) see PCR2 in Table 5) containing no fluorophores, each at 1 mM concentration.

A detection oligonucleotide designated PCR2-1 (5'-GCAAGATGGAGGAA ACAAFGGCTGGAGCCAA-3' (SEQ ID NO:44) was also included in the reaction mixture at concentrations of 0.2 or 0.5 mM. The results are illustrated in FIG. 1. The graphs labeled $A_{test}$ and $B_{test}$ are amplified in the presence of 0.2 nM and 0.5 mM label oligonucleotide, respectively. The graphs labeled $A_{ctrl}$ and $B_{ctrl}$ are controls; the same reaction mixture absent thermocycling. The label oligonucleotide provided a clear signal indicating the presence of amplification product.

(XVIII)

5'-GTG TGG AAA ATC TCT AGC AGT-3' (SEQ ID NO:46)
  |||  |||  |||  |||  |||  |||  |||
3'-CAC ACC TTT TAG AGA TCF TCA-5' (SEQ ID NO:47)--

The HIV-1 integrase protein was titrated into the above solution (0–520 nM), measuring anisotropy changes with each addition (along with the appropriate controls). The reaction was done at 20° C. to prevent the normal HIV-1 integrase cleavage reaction from occurring. When the protein was added to the oligonucleotide, the signal went off scale. This suggests that there was a disruption of base stacking (which causes the quench) in the vicinity of the fluorophore. It is believed that the DNA underwent tertiary structure distortion upon binding to the HIV-1 integrase protein. The fluorescent nucleotide, being located within the area of distortion, was dequenched thereby facilitating detection of the fluorescence signal.

TABLE 5

Illustration of the Pax3 region serving as template and
the various primers used to amplify and detect amplification products
(SEQ ID NO:45). Complementary sequence = SEQ ID NO:22.

```
              PCR1
5'-acc tca gtc aga tga agg ctc cga tat tga ctc tga acc tga ttt acc gct
3'-tgg agt cag tct act tcc gag gct ata act gag act tgg act aaa tgg cga gaa Gag gaa gca gcg cag gag cag aac cca cct tca cgg cag agc agc tgg agg
ctt ctc ctt cgt cgc gtc ctc gtc ttg ggt gga agt gcc gtc tcg tcg acc tcc acc Tgg agc ggg ctt tcg aga gaa ccc act acc cag aca ttt aca cca ggg agg
ttg acC TCG CCC GAAFAGC TCT CTt ggg tga tgg gtc tgt aaa tgt ggt ccc tcc
             PCR6 aag ctg gcc cag agg gcg aag ctt acc gag gcc cga gtg cag gtc tgg ttt agc
ttc gac cgg gtc tcc cgc ttc gaa tgg ctc cgg gct cac gtc cag acc aaa tcg PCR2-1
aac cgc cgt GCA AGA TGG AGG AAA CAA F GGC TGG ACG CAA tca act gat ggc ttt
ttg gcg gca cgt tct acc tcc ttt gtt    ccg acc tgc gtt agt tga cta ccg aaa caa cca tct cat tcc ggg ggg att ccc tcc cac cgc cat gcc gac cct gcc aac
gtt ggt aga gta agg ccc ccc taa ggg agg gtg gcg gta cgg ctg gga cgg ttg PCR4
aat acc agc tgt cgg agc act ctt acc agc cca cgt ctA TTC CAC AAFG CCG TGT
tta tgg tcg aca gcc tcg tga gaa tgg tcg ggt gca gat aag gtg tt c ggc aca PCR2
CAg atc ccA GTA GCA CCG TCC ACA GAC CCT CAg-3'
gtc tag ggt cat cgt ggc agg tgt ctg gga gtc-5'
```

Example 4

Detection of DNA/Protein Binding

A buffer solution was prepared containing a double stranded label oligonucleotide selected to act as a target substrate for HIC integrase. The buffer solution included 25 nM (MOPS, pH 7.2, 50 mM NaCl, 7.5 mM $MnCl_2$, 10 m M 2-mercaptoethanol, 100 mg/ml BSA, (10% w/v) glycerol, 100–175 nM of the label oligonucleotide as shown in Formula XVIII.

Example 5

Use of Label Oligonucleotides with Restriction Digests

As indicated above, the label oligonucleotides can be used to identify the presence or absence of a particular genetic sequence within a mixture. In one embodiment, the mixture under investigation could be genomic DNA or mRNA isolated from cells in culture, from tissue, or amplified from a biological sample. One problem with using short probes to bind to large genomic sized DNA is that at temperatures lower than 95° C., the larger DNA is highly favored in binding.

In order to shift the binding equilibrium of the fluorophore containing probe (maybe a 20–30-mer) to offset the tremendous advantage of the annealed genomic DNA, restriction sites which bracket the selected target probe site will be digested with the appropriate restriction endonucleases. Restriction sites are quite abundant throughout most gene sequences. By constructing the label oligonucleotide probe to be substantially complementary to the sequence between two selected restriction sites, the fluorophore containing oligonucleotide will have a greatly enhanced chance of binding. An excess of the probe will shift the equilibrium even further in its favor.

The nMyc gene was used as a model for this system. This gene is overexpressed in many tumors and there are cell lines which express a single copy or amplified copies of the gene.

The sequence of the nMyc gene is illustrated in SEQ ID NO:16 and FIG. 2. Sites that are appropriate for insertion of the fluorophore are in bold. A restriction site map of the gene reveals sites which bracket the fluorophore insertion site resulting in a sequence of 20–38 bases for each site. For example, the sites for RD9 which is located between bases 896 and 922, are illustrated.

The arrows mark the restriction sites for Alu 1 and Hga 1. Pairing of this 26 mer with a complementary sequence (such as the one generated by digestion of the gene by the above mentioned restriction enzymes) resulted in up to a 14 fold increase in the fluorescence signal. Other suitable label oligonucleotides include the probes shown in Table 6. Each of the oligonucleotides listed below is being tested as a hybridization probe after digestion of genomic DNA with the appropriate restriction enzymes.

This strategy has been applied to the detection of HIV-1 PCR products generated by two different sets of primers. Restriction sites were selected and probes were synthesized identical to the restriction fragments framed by the restriction enzymes only with the addition of the fluorophore. The fluorescence intensity of positive PCR product from plasmid containing 1×10⁵ virus copies/μg DNA versus the PCR product from 1 μg human genomic uninfected DNA was 3- to 5-fold greater.

Figure 3:
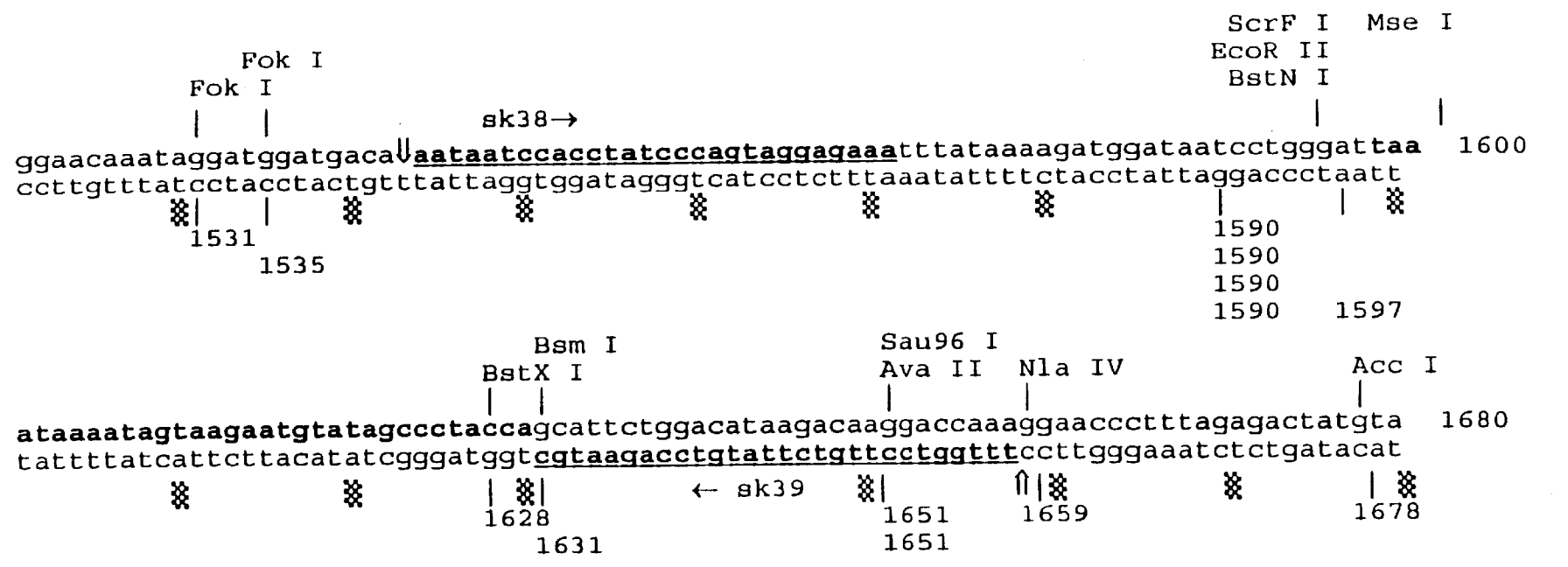

FIG. 3 shows a sequence selected from the HXB2 plasmid standard which is detected using a label oligonucleotide. The label oligonucleotide was designed to specifically bind to a PCR product from the HXB2 plasmid which is amplified by the SK38 and SK39 primers which are underlined and bold in the map (FIG. 3). The Mse I and BsM I digestion of the amplification product results in production of the restriction fragment (5'-taa ata aaa tag taa gaa tgt ata gcc cta cca-3'; SEQ ID NO:59) designated HIVPCR.

Insertion of a fluorophore (3-methyl isoxanthopterin) into an identical sequence produces a probe (5'-taa ata aFa tag taa gaa tgt ata gcc cta cca-3'; SEQ ID NO:60, designated HIVPCRF) that increases in its fluorescence intensity (approximately 5 fold) upon binding to its complement (HIVPCR).

The fluorescence enhancement upon binding is believed to occur because of a reduction of quenching effects from the neighboring bases due to a disruption of base stacking interactions.

This example illustrates that target nucleic acids can be directly detected (e.g., after amplification) without the need to separate the probes on a gel. This provides a highly efficient method for detection and/or quantification of particular nucleic acids, e.g., in diagnostic applications.

It is understood that the examples and embodiments described herein are for illustrative purposes only and that various modifications or changes in light thereof will be suggested to persons skilled in the art and are to be included within the purview of this application and scope of the appended claims. All publications, patents, and patent applications cited herein are hereby incorporated by reference for all purposes.

TABLE 6

Probes suitable for detection of nMYC and subsequences thereof. Appropriate restriction enzymes to increase probe binding and resulting signal level are also shown.

| Probe | Sequence | Restriction Sites | SEQ ID No |
|---|---|---|---|
| RD1 | ca gaFaaccacaa cat | Fok I - Sso II | 48 |
| RD2 | ctt ttgctggaaFa aggaaa | Alu I ※ Tsp 509 | 49 |
| RD3 | cggagttggtaaFaga atgagaagg | Msp I - Pal I | 50 |
| RD4 | tagacgct tctcaaFaact ggaca | Mae I - Mae III | 51 |
| RD5 | agaagaagata aFagagcgagg cgt<u>cccca</u> | Fok 1 - Mae II | 52 |
| RD6 | 5'-aaaaaaaaa tcaaFaatgtg caaagtggca g-3' | Alw N1 - Mse 1 | 53 |
| RD7 | 5'-cctga gcgtgagaFaa gctggac-3' | Sau 961 ※ Sau 961 | 54 |
| RD8 | 5'-cctttt tcaaFaatgac caccttg-3' | Sty I - Hae I | 55 |
| RD9 | cttg agcccccgaFa actctgactc gg | Alu I - Hga I | 56 |
| RD10 | 5'-aaaaaaaFaa tcaaaatgtg caaFagtggcag-3' | AlwNI - Mse I | 57 |
| RD11 | agcagt tgctaaagaa Faattgaacac gctcggactt gc | Fnu4HI ※ Mae I | 58 |

What is claimed is:

1. A method of detecting the presence, absence, or quantity of a target nucleic acid, said method comprising the steps of:
   contacting said target nucleic acid with a nucleic acid probe wherein said nucleic acid probe comprises a fluorescent nucleotide located in said probe such that, when said probe, hybridizes to said target nucleic acid the fluorescent nucleotide is in a loop that does no participate in complementary base pairing with a nucleotide of said target nucleic acid; and
   detecting the fluorescence produced by said fluorescent nucleotide, when said probe is hybridized to said target nucleic acid.

2. A oligonucleotide comprising a fluorescent nucleotide wherein said oligonucleotide is hybridized to a target nucleic acid forming a hybrid duplex in which said fluorescent nucleotide does not participate in complementary base pairing with a nucleotide of said target nucleic acid, further wherein said fluorescent nucleotide does not interact with a second fluorophore.

3. The method of claim 1, wherein said loop ranges in length from about 1 to about 100 nucleotides when said probe hybridizes to said target nucleic acid.

4. The method of claim 3, wherein said loop is an insertion in said nucleic acid probe which probe is complementary to said target nucleic acid or to a contiguous subsequence of said target nucleic acid, and further wherein said loop is not complementary to said target nucleic acid or to a contiguous subsequence of said target nucleic acid.

5. The method of claim 4, wherein said insertion is three nucleotides in length and comprises two nucleotides each adjacent to said fluorescent nucleotide in addition to said fluorescent nucleotide.

6. The method of claim 4, wherein at least one nucleotide adjacent to said fluorescent nucleotide is a purine.

7. The method of claim 6, wherein at least one nucleotide adjacent to said fluorescent nucleotide is an adenosine.

8. The method of claim 6, wherein said fluorescent nucleotide is bordered by at least two adjacent purines in both the 5' and 3' direction.

9. The method of claim 8, wherein said adjacent purines are adenosine.

10. The method of claim 4, wherein said insertion is said fluorescent nucleotide.

11. The method of claim 4, wherein said insertion is self-complementary and forms a hairpin wherein said fluorescent nucleotide is present in the loop of said hairpin and does not participate in complementary base pairing.

12. The method of claim 3, wherein the nucleotides comprising said loop are selected such that they are not complementary to the corresponding nucleotides of the target nucleic acid when said probe is hybridized to said target nucleic acid and wherein said probe is complementary to at least two non-contiguous subsequences of said target nucleic acid.

13. The method of claim 1, wherein said fluorescent nucleotide is present in a terminal subsequence of said nucleic acid probe, wherein said terminal subsequence does not hybridize to said target nucleic acid when said nucleic acid probe hybridizes to said target nucleic acid.

14. The method of claim 13, wherein said terminal subsequence forms a terminal hairpin by hybridization with a second subsequence of said probe such that said fluorescent nucleotide is present in a loop of said hairpin and does not participate in complementary base pairing.

15. The method of claim 1, wherein said detecting comprises detecting an increase in fluorescence of said fluorescent nucleotide when said probe forms a hybrid duplex, with said target nucleic acid.

16. The method of claim 1, wherein said fluorescent nucleotide is selected from the group consisting of a pteridine nucleotide, a lumazine nucleotide, 3-methyl-8-(2-deoxy-β-D-ribofuranosyl) isoxanthopterin, and 6-methyl-8-(2-deoxy-β-D-ribofuranosyl) isoxanthopterin.

17. The method of claim 16, wherein said fluorescent nucleotide is selected from the group consisting of 2-amino-2-phenyl-8-(2-deoxy-β-D-ribofuranosyl)pteridine-7-one, 4-amino-6-phenyl-8-(2-deoxy-β-D-ribofuranosyl)-pteridine-7-one, 3-methyl-8-(2-deoxy-β-D-ribofuranosyl) isoxanthopterin, 2'-deoxy-β-D-ribofuranosyl-isoxanthopterin, 2-amino-6-methyl-4-oxo-8-(2-deoxy-β-D-ribofuranosyl)-pteridine-7-one, 6,7-dimethyl-4-amino-1-(2-deoxy-β-D-ribofuranosyl)-pteridine-2-one, 4-amino-1-(2-deoxy-β-D-ribofuranosyl)-7-methyl-pteridine-2-one, 4-amino-1-(2-deoxy-β-D-riobfuranosyl)-6-methyl-pteridine-2-one, and 2-amino-1-(2-deoxy-β-D-ribofuranosyl)-pteridine-2-one.

18. The method of claim 16, wherein said fluorescent nucleotide is 2 amino purine.

19. The method of claim 1, wherein said method further comprises cutting said target nucleic acid to an average length of between about twenty times as long as said nucleic acid probe to about one times as long as said probe.

20. The method of claim 19, wherein said characteristic average length is approximately the length of said nucleic acid probe.

21. The method of claim 19, wherein said cutting is by treatment with a restriction endonuclease.

22. The label of claim 2, wherein said fluorescent nucleotide is present in a subsequence of said probe that forms a loop ranging in length from about 1 to about 100 nucleotides, when said probe hybridizes to said target nucleic acid.

23. The label of claim 22, wherein said loop is an insertion in said nucleic acid probe which probe is complementary to said target nucleic acid or to a contiguous subsequence of said target nucleic acid, and further wherein said loop is not complementary to said target nucleic acid or to a contiguous subsequence of said target nucleic acid.

24. The label of claim 23, wherein said at least one nucleotide adjacent to said fluorescent nucleotide is a purine.

25. The label of claim 23, wherein said insertion is three nucleotides in length and comprises two nucleotides each adjacent to said fluorescent nucleotide in addition to said fluorescent nucleotide.

26. The label of claim 23, wherein said insertion is said fluorescent nucleotide.

27. The label of claim 23, wherein said insertion is self-complementary and forms a hairpin wherein said fluorescent nucleotide is present in the loop of said hairpin and does not participate in complementary base pairing.

28. The label of claim 22, wherein said loop comprises contiguous nucleotides selected such that they are not complementary to the corresponding nucleotides of the target nucleic acid when said probe is hybridized to said target nucleic acid and wherein said probe is complementary to at least two non-contiguous subsequences of said target nucleic acid.

29. The label of claim 2, wherein said fluorescent nucleotide is present in a terminal subsequence of said nucleic acid probe, wherein said terminal subsequence does not hybridize to said target nucleic acid when said nucleic acid probe hybridizes to said target nucleic acid.

30. The label of claim 29, wherein said terminal subsequence forms a terminal hairpin by hybridization with a second subsequence of said probe such that said fluorescent nucleotide is present in a loop of said hairpin and does not participate in complementary base pairing.

31. The label of claim 2, wherein said fluorescent nucleotide is selected from the group consisting of a pteridine nucleotide, a lumazine nucleotide, 2 amino purine, 3-methyl-8-(2-deoxy-β-D-ribofuranosyl)isoxanpterin, and 6-methyl-8-(2-deoxy-β-D-ribofuranosyl) isoxanthopterin.

32. The label of claim 2, wherein said fluorescent nucleotide is selected from the group consisting of 2-amino-2-phenyl-8-(2-deoxy-β-D-ribofuranosyl)pteridine-7-one, 4-amino-6-phenyl-8-(2-deoxy-β-D-ribofuranosyl)p-pteridine-7-one, 3-methyl-8-(2-deoxy-β-D-ribofuranosyl) isoxanthopterin, 2'-deoxy-β-D ribofuranosyl-isoxanthopterin, 2-amino-6-methyl-4-oxo-8-(2-deoxy-β-D-ribofuranosyl)-pteridine-7-one, 6,7-dimethyl-4-amino-1-(2-deoxy-β-D-ribofuranosyl)-pteridine-2-one, 4-amino-1-(2-deoxy-β-D-ribofuranosyl)-7-methyl-pteridine-2-one, 4-amino-1-(2-deoxy-β-D-riobfuranosyl)-6-methyl-pteridine-2-one, and 2-amino-1-(2-deoxy-β-D-ribofuranosyl)-pteridine-2-one.

33. The label of claim 31, wherein said fluorescent nucleotide is 2 amino purine.

34. The label of claim 2, wherein said fluorescent nucleotide is 3-methyl-8-(2-deoxy-β-D-ribofuranosyl) isoxanthopterin.

35. A kit comprising a container containing a fluorescent label of claim 2.

* * * * *

SEQUENCE LISTING (1) GENERAL INFORMATION:

(iii) NUMBER OF SEQUENCES: 68

(2) INFORMATION FOR SEQ ID NO: 1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 1:

ATTCCACAAN GCCGTGTCA                                                  19

(2) INFORMATION FOR SEQ ID NO: 2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 2:

GGCTGGTAAN GAGTGCTCC                                                  19

(2) INFORMATION FOR SEQ ID NO: 3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 3:

TCTCTCGAAN AGCCCGCTC                                                  19

(2) INFORMATION FOR SEQ ID NO: 4:

(i) SEQUENCE CHARACTERISTICS:
        (A) LENGTH: 19 base pairs
        (B) TYPE: nucleic acid (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 4:

ACCGCTGAAN GAGGAAGCA                                                        19

(2) INFORMATION FOR SEQ ID NO: 5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 17
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 5:

CCTCTAAGAG GTGTGTNGGT GTGGAGAATC TCC                                        33

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 19
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 6:

GCAAGATGGA GGAAACAANG GCTGGAGCCA A                                          31

(2) INFORMATION FOR SEQ ID NO: 7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 13
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(ix) FEATURE:

```
         (A) NAME/KEY: modified_base
         (B) LOCATION: 20
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(xi) SEQUENCE DESCRIPTION: SEQ ID NO: 7:

GCAAGATGGA GGNAAACAAN GGCTGGAGCC AA                                       32

(2) INFORMATION FOR SEQ ID NO: 8:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 5
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(ix) FEATURE:
         (A) NAME/KEY: modified_base
         (B) LOCATION: 14
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(ix) FEATURE:
         (A) NAME/KEY: modified_base
         (B) LOCATION: 21
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(xi) SEQUENCE DESCRIPTION: SEQ ID NO: 8:

GCAANGATGG AGGNAAACAA NGGCTGGAGC CAA                                      33

(2) INFORMATION FOR SEQ ID NO: 9:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 5
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(ix) FEATURE:
         (A) NAME/KEY: modified_base
         (B) LOCATION: 14
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(ix) FEATURE:
         (A) NAME/KEY: modified_base
         (B) LOCATION: 21
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(ix) FEATURE:
```

```
        (A) NAME/KEY: modified_base
        (B) LOCATION: 28
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 9:

GCAANGATGG AGGNAAACAA NGGCTGGNAG CCAA                               34

(2) INFORMATION FOR SEQ ID NO: 10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 5
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(ix) FEATURE:
        (A) NAME/KEY: modified_base
        (B) LOCATION: 20
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 10:

GCAANGATGG AGGAAACAAN GGCTGGAGCC AA                                 32

(2) INFORMATION FOR SEQ ID NO: 11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 13
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 11:

CGGCAGAGCT GGNAGGAACT GGAGCGGG                                      28

(2) INFORMATION FOR SEQ ID NO: 12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 7
        (D) OTHER INFORMATION: /mod_base= OTHER
            /note= "N = 3-methyl-8-(2-deoxy-beta-D-ribofuranosyl)
            isoxanthopterin fluorescent nucleotide analogue"
```

```
    (ix) FEATURE:
         (A) NAME/KEY: modified_base
         (B) LOCATION: 14
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(xi) SEQUENCE DESCRIPTION: SEQ ID NO: 12:

CGGCAGNAGC TGGNAGGAAC TGGAGCGGG                                        29

(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: modified_base
         (B) LOCATION: 7
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(ix) FEATURE:
         (A) NAME/KEY: modified_base
         (B) LOCATION: 14
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(ix) FEATURE:
         (A) NAME/KEY: modified_base
         (B) LOCATION: 24
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(xi) SEQUENCE DESCRIPTION: SEQ ID NO: 13:

CGGCAGNAGC TGGNAGGAAC TGGNAGCGGG                                       30

(2) INFORMATION FOR SEQ ID NO: 14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: modified_base
         (B) LOCATION: 10
         (D) OTHER INFORMATION: /mod_base= OTHER
             /note= "N = 3-methyl-8-(2-deoxy-beta-D-ribofuranosyl)
             isoxanthopterin fluorescent nucleotide analogue"

(xi) SEQUENCE DESCRIPTION: SEQ ID NO: 14:

ACCGCTGAAN GAGGAAGCA                                                   19

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA
```

(ix) FEATURE:
    (A) NAME/KEY: modified_base
    (B) LOCATION: 10
    (D) OTHER INFORMATION: /mod_base= OTHER
        /note= "N = 3-methyl-8-(2-deoxy-beta-D-ribofuranosyl)
        isoxanthopterin fluorescent nucleotide analogue"

(xi) SEQUENCE DESCRIPTION: SEQ ID NO: 15:

ACCGCTGAAN GAGGAANGCA                                          20

(2) INFORMATION FOR SEQ ID NO: 16:

(i) SEQUENCE CHARACTERISTICS:
        (A) LENGTH: 1284 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

AGCTCCGAGC CCCCGAGCTG GGTCACGGAG ATGCTGCTTG AGAACGAGCT GTGGGGCAGC    60

CCGGCCGAGG AGGACGCGTT CGGCCTGGGG GGACTGGGTG GCCTCACCCC CAACCCGGTC   120

ATCCTCCAGG ACTGCATGTG GAGCGGCTTC TCCGCCCGCG AGAAGCTGGA GCGCGCCGTG   180

AGCGAGAAGC TGCAGCACGG CCGCGGGCCG CCAACCGCCG GTTCCACCGC CCAGTCCCCG   240

GGAGCCGGCC CCGCCAGCCC TGCGGGTCGC GGGCACGGCG GGGCTGCGGG AGCCGGCCGC   300

GCCGGGGCCG CCCTGCCCGC CGAGCTCGCC CACCCGGCCG CCGAGTGCGT GGATCCCGCC   360

GTGGTCTTCC CCTTTCCCGT GAACAAGCGC GAGCCAGCGC CCGTGCCCGC AGCCCCGGCC   420

AGTGCCCCGG CGGCGGGCCC TGCGGTCGCC TCGGGGCGG GTATTGCCGC CCCAGCCGGG   480

GCCCGGGGG TCGCCCCTCC GCGCCCAGGC GGCCGCCAGA CCAGCGGCGG CGACCACAAG   540

GCCCTCAGTA CCTCCGGAGA GGACACCCTG AGCGATTCAG ATGATGAAGA TGATGAAGAG   600

GAAGATGAAG AGGAAGAAAT CGACGTGGTC ACTGTGGAGA AGCGGCGTTC CTCCTCCAAC   660

ACCAAGGCTG TCACCACATT CACCATCACT GTGCGTCCCA AGAACGCAGC CCTGGGTCCC   720

GGGAGGGCTC AGTCCAGCGA GCTGATCCTC AAACGATGCC TTCCCATCCA CCAGCAGCAC   780

AACTATGCCG CCCCCTCCCC CTACGTGGAG AGTGAGGATG CACCCCCACA GAAGAAGATA   840

AAGAGCGAGG CGTCCCCACG TCCGCTCAAG AGTGTCATCC CCCCAAAGGC TAAAGGCTTG   900

AGCCCCCGAA ACTCTGACTC GGAGGACAGT GAGCGTCGCA GAAACCACAA CATCCTGGAG   960

CGCCAGCGCC GCAACGACCT TCGGTCCAGC TTTCTCACGC TCAGGGACCA CGTGCCGGAG  1020

TTGGTAAAGA ATGAGAAGGC CGCCAAGGTG GTCATTTTGA AAAAGGCCAC TGAGTATGTC  1080

CACTCCCTCC AGGCCGAGGA GCACCAGCTT TTGCTGGAAA AGGAAAAATT GCAGGCAAGA  1140

CAGCAGCAGT TGCTAAAGAA AATTGAACAC GCTCGGACTT GCTAGACGCT TCTCAAAACT  1200

GGACAGTCAC TGCCACTTTG CACATTTTGA TTTTTTTTTT AAACAAACAT TGTGTTGACA  1260

TTAAGAATGT TGGTTTACTT TCAA                                      1284

(2) INFORMATION FOR SEQ ID NO: 17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
    (A) NAME/KEY: modified_base
    (B) LOCATION: 17
    (D) OTHER INFORMATION: /mod_base= OTHER
        /note= "N = 3-methyl-8-(2-deoxy-beta-D-ribofuranosyl)
        isoxanthopterin fluorescent nucleotide analogue"

(xi) SEQUENCE DESCRIPTION: SEQ ID NO: 17:

CCTCTAAGAG GTGTGTNGGT GTGGAGAATC TCC         33

(2) INFORMATION FOR SEQ ID NO: 18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

GGAGATTCTC CACACACCAC ACCTCTTAGA GG          32

(2) INFORMATION FOR SEQ ID NO: 19:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

GGAACAAATA GGATGGATGA CAAATAATCC ACCTATCCCA GTAGGAGAAA TTTATAAAAG    60

ATGGATAATC CTGGGATTAA ATAAAATAGT AAGAATGTAT AGCCCTACCA GCATTCTGGA   120

CATAAGACAA GGACCAAAGG AACCCTTTAG AGACTATGTA                         160

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

GGAGATTCTC CACACCACAA CTCTTAGAGG             30

(2) INFORMATION FOR SEQ ID NO: 21:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 17
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 21:

CCTCTAAGAG GTGTGTNGTG TGGAGAATCT CC                                              32

(2) INFORMATION FOR SEQ ID NO: 22:

(i) SEQUENCE CHARACTERISTICS:
        (A) LENGTH: 409 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 289
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 22:

CTGAGGGTCT GTGGACGGTG CTACTGGGAT CTGACACGGC TTGTGGAATA GACGTGGGCT      60

GGTAAGAGTG CTCCGACAGC TGGTATTGTT GGCAGGGTCG GCATGGCGGT GGGAGGGAAT     120

CCCCCCGGAA TGAGATGGTT GAAAGCCATC AGTTGATTGG CTCCAGCCTT GTTTCCTCCA     180

TCTTGCACGG CGGTTGCTAA ACCAGACCTG CACTCGGGCC TCGGTAAGCT TCGCCCTCTG     240

GGCCAGCTTC CTCCCTGGTG TAAATGTCTG GGTAGTGGGT TCTCTCGANA AGCCCGCTCC     300

AGTTCCTCCA GCTGCTCTGC CGTGAAGGTG GGTTCTGCTC CTGCGCTGCT TCCTCTTCAG     360

CGGTAAATCA GGTTCAGAGT CAATATCGGA GCCTTCATCT GACTGAGGT                409

(2) INFORMATION FOR SEQ ID NO: 23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 17
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 23:

CCTCTAAGAG GTGTACNAGT GTGGAGAATC TCC                                             33

(2) INFORMATION FOR SEQ ID NO: 24:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

GGAGATTCTC CACACTGTAC ACCTCTTAGA GG                                              32

(2) INFORMATION FOR SEQ ID NO: 25:

(i) SEQUENCE CHARACTERISTICS:

(A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 17
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 25:

CCTCTAAGAG GTGTAANAGT GTGGAGAATC TCC                33

(2) INFORMATION FOR SEQ ID NO: 26:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

GGAGATTCTC CACACTTTAC ACCTCTTAGA GG                 32

(2) INFORMATION FOR SEQ ID NO: 27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 17
        (D) OTHER INFORMATION: /mod_base= OTHER
            /note= "N = 3-methyl-8-(2-deoxy-beta-D-ribofuranosyl)
            isoxanthopterin fluorecent nucleotide analogue"

(xi) SEQUENCE DESCRIPTION: SEQ ID NO: 27:

CCTCTAAGAG GTGTCCNCCT GTGGAGAATC TCC                33

(2) INFORMATION FOR SEQ ID NO: 28:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

GGAGATTCTC CACAGGGGAC ACCTCTTAGA GG                 32

(2) INFORMATION FOR SEQ ID NO: 29:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
            (A) NAME/KEY: modified_base
            (B) LOCATION: 13
            (D) OTHER INFORMATION: /mod_base= OTHER
                /note= "N = 3-methyl-8-(2-deoxy-beta-D-ribofuranosyl)
                isoxanthopterin fluorescent nucleotide analogue"

(xi) SEQUENCE DESCRIPTION: SEQ ID NO: 29:

GGCTTTCGAG AGNAACCCAC TACCCA                                26

(2) INFORMATION FOR SEQ ID NO: 30:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 30:

TGGGTAGTGG GTTCTCTCGA AAGCC                                 25

(2) INFORMATION FOR SEQ ID NO: 31:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 17
            (D) OTHER INFORMATION: /mod_base= OTHER
                /note= "N = 3-methyl-8-(2-deoxy-beta-D-ribofuranosyl)
                isoxanthopterin fluorescent nucleotide analogue"

(xi) SEQUENCE DESCRIPTION: SEQ ID NO: 31:

CCTCTAAGAG GTGTAANAAT GTGGAGAATC TCC                        33

(2) INFORMATION FOR SEQ ID NO: 32:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 32:

GGAGATTCTC CACATTTTAC ACCTCTTATA GG                         32

(2) INFORMATION FOR SEQ ID NO: 33:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 13

```
            (D) OTHER INFORMATION: /mod_base= OTHER
                /note= "N = 2-amino purine fluorescent nucleotide
                analogue"

(xi) SEQUENCE DESCRIPTION: SEQ ID NO: 33:

GGCTTTCGAG AGNAACCCAC TACCCA                                      26

(2) INFORMATION FOR SEQ ID NO: 34:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 19
        (D) OTHER INFORMATION: /mod_base= OTHER
            /note= "N = 2-amino purine fluorescent nucleotide
            analogue"

(xi) SEQUENCE DESCRIPTION: SEQ ID NO: 34:

GCAAGATGGA GGAAACAANG GCTGGAGCCA A                                31

(2) INFORMATION FOR SEQ ID NO: 35:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 7
        (D) OTHER INFORMATION: /mod_base= OTHER
            /note= "N = 2-amino purine fluorescent nucleotide
            analogue"

(xi) SEQUENCE DESCRIPTION: SEQ ID NO: 35:

GCAAGANTGG AGGAAACAAG GCTGGAGCCA A                                31

(2) INFORMATION FOR SEQ ID NO: 36:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 19
        (D) OTHER INFORMATION: /mod_base= OTHER
            /note= "N = 2-amino purine fluoresent nucleotide
            analogue"

(xi) SEQUENCE DESCRIPTION: SEQ ID NO: 36:

CGGCAGAGCA GCTGGAGGNA ACTGGAGCGG G                                31

(2) INFORMATION FOR SEQ ID NO: 37:

(i) SEQUENCE CHARACTERISTICS:
        (A) LENGTH: 31 base pairs
```

```
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = 2-amino purine fluorescent nucleotide
            analogue"

(xi) SEQUENCE DESCRIPTION: SEQ ID NO: 37:

CGGCAGAGCN AGCTGGAGGA ACTGGAGCGG G                              31

(2) INFORMATION FOR SEQ ID NO: 38:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = 2-amino purine fluorescent nucleotide
            analogue"

(xi) SEQUENCE DESCRIPTION: SEQ ID NO: 38:

ATTCCACAAN GCCGTGTCA                                            19

(2) INFORMATION FOR SEQ ID NO: 39:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = 2-amino purine fluorescent nucleotide
            analogue"

(xi) SEQUENCE DESCRIPTION: SEQ ID NO: 39:

GGCTGGTAAN GAGTGCTCC                                            19

(2) INFORMATION FOR SEQ ID NO: 40:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = 2-amino purine fluorescent nucleotide
            analogue"
```

(xi) SEQUENCE DESCRIPTION: SEQ ID NO: 40:

TCTCTCGAAN AGCCCGCTC                                            19

(2) INFORMATION FOR SEQ ID NO: 41:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = 2-amino purine fluorescent nucleotide
            analogue"

(xi) SEQUENCE DESCRIPTION: SEQ ID NO: 41:

ACCGCTGAAN GAGGAAGCA                                            19

(2) INFORMATION FOR SEQ ID NO: 42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 42:

ACCTCAGTCA GATGAAGGCT CCGAT                                     25

(2) INFORMATION FOR SEQ ID NO: 43:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 43:

AGTAGCACCG TCCACAGACC CTCAG                                     25

(2) INFORMATION FOR SEQ ID NO: 44:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 19
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 44:

GCAAGATGGA GGAAACAANG GCTGGAGCCA A                              31

(2) INFORMATION FOR SEQ ID NO: 45:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 241
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(ix) FEATURE:
        (A) NAME/KEY: modified_base
        (B) LOCATION: 370
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 45:

```
ACCTCAGTCA GATGAAGGCT CCGATATTGA CTCTGAACCT GATTTACCGC TGAAGAGGAA      60

GCAGCGCAGG AGCAGAACCC ACCTTCACGG CAGAGCAGCT GGAGGAACTG GAGCGGGCTT     120

TCGAGAGAAC CCACTACCCA GACATTTACA CCAGGGAGGA AGCTGGCCCA GAGGGCGAAG     180

CTTACCGAGG CCCGAGTGCA GGTCTGGTTT AGCAACCGCC GTGCAAGATG GAGGAAACAA     240

NGGCTGGAGC CAATCAACTG ATGGCTTTCA ACCATCTCAT TCCGGGGGGA TTCCCTCCCA     300

CCGCCATGCC GACCCTGCCA ACAATACCAG CTGTCGGAGC ACTCTTACCA GCCCACGTCT     360

ATTCCACAAN GCCGTGTCAG ATCCCAGTAG CACCGTCCAC AGACCCTCAG              410
```

(2) INFORMATION FOR SEQ ID NO: 46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 46:

```
GTGTGGAAAA TCTCTAGCAG T                                              21
```

(2) INFORMATION FOR SEQ ID NO: 47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 4
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 47:

```
ACTNCTAGAG ATTTTCCACA C                                              21
```

(2) INFORMATION FOR SEQ ID NO: 48:

```
    (i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 5
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 48:

CAGANAACCA CAACAT                                                    16

(2) INFORMATION FOR SEQ ID NO: 49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 13
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 49:

CTTTTGCTGG AANAAGGAAA                                                20

(2) INFORMATION FOR SEQ ID NO: 50:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 13
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 50:

CGGAGTTGGT AANAGAATGA GAAGG                                          25

(2) INFORMATION FOR SEQ ID NO: 51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 15
        (D) OTHER INFORMATION: /mod_base= OTHER
```

/note= "N = 3-methyl-8-(2-deoxy-beta-D-ribofuranosyl)
                    isoxanthopterin fluorescent nucleotide analogue"

(xi) SEQUENCE DESCRIPTION: SEQ ID NO: 51:

TAGACGCTTC TCAANAACTG GACA                                              24

(2) INFORMATION FOR SEQ ID NO: 52:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 13
         (D) OTHER INFORMATION: /mod_base= OTHER
             /note= "N = 3-methyl-8-(2-deoxy-beta-D-ribofuranosyl)
                    isoxanthopterin fluorescent nucleotide analogue"

(xi) SEQUENCE DESCRIPTION: SEQ ID NO: 52:

AGAAGAAGAT AANAGAGCGA GGCGTCCCCA                                        30

(2) INFORMATION FOR SEQ ID NO: 53:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 14
         (D) OTHER INFORMATION: /mod_base= OTHER
             /note= "N = 3-methyl-8-(2-deoxy-beta-D-ribofuranosyl)
                    isoxanthopterin fluorescent nucleotide analogue"

(xi) SEQUENCE DESCRIPTION: SEQ ID NO: 53:

AAAAAAAAAT CAANAATGTG CAAAGTGGCA G                                      31

(2) INFORMATION FOR SEQ ID NO: 54:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 14
         (D) OTHER INFORMATION: /mod_base= OTHER
             /note= "N = 3-methyl-8-(2-deoxy-beta-D-ribofuranosyl)
                    isoxanthopterin fluorescent analogue"

(xi) SEQUENCE DESCRIPTION: SEQ ID NO: 54:

CCTGAGCGTG AGANAAGCTG GAC                                               23

(2) INFORMATION FOR SEQ ID NO: 55:

(i) SEQUENCE CHARACTERISTICS:
         (A) LENGTH: 24 base pairs
         (B) TYPE: nucleic acid (C) STRANDEDNESS: single
        (D) TOPOLOGY: linear (ii) MOLECULE TYPE: DNA (ix) FEATURE:
        (A) NAME/KEY: modified_base
        (B) LOCATION: 11
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 55:

CCTTTTTCAA NAATGACCAC CTTG                                              24

(2) INFORMATION FOR SEQ ID NO: 56:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 14
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 56:

CTTGAGCCCC CGANAACTCT GACTCGG                                           27

(2) INFORMATION FOR SEQ ID NO: 57:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 8
        (D) OTHER INFORMATION: /mod_base= OTHER
            /note= "N = 3-methyl-8-(2-deoxy-beta-D-ribofuarosyl)
            isoxanthopterin fluorescent nucleotide analogue"

(ix) FEATURE:
        (A) NAME/KEY: modified_base
        (B) LOCATION: 24
        (D) OTHER INFORMATION: /mod_base= OTHER
            /note= "N = 3-methyl-8-(2-deoxy-beta-D-ribofuranosyl)
            isoxanthopterin fluorescent nucleotide analogue"

(xi) SEQUENCE DESCRIPTION: SEQ ID NO: 57:

AAAAAAANAA TCAAAATGTG CAANAGTGGC AG                                     32

(2) INFORMATION FOR SEQ ID NO: 58:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (ix) FEATURE:

```
            (A) NAME/KEY: modified_base
            (B) LOCATION: 17
            (D) OTHER INFORMATION: /mod_base= OTHER
                /note= "N = 3-methyl-8-(2-deoxy-beta-D-ribofuranosyl)
                isoxanthopterin fluorescent nucleotide analogue"

(xi) SEQUENCE DESCRIPTION: SEQ ID NO: 58:

AGCAGTTGCT AAAGAANAAT TGAACACGCT CGGACTTGC                                39

(2) INFORMATION FOR SEQ ID NO: 59:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 59:

TAAATAAAAT AGTAAGAATG TATAGCCCTA CCA                                      33

(2) INFORMATION FOR SEQ ID NO: 60:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 8
            (D) OTHER INFORMATION: /mod_base= OTHER
                /note= "N = 3-methyl-8-(2-deoxy-beta-ribofuranosyl)
                isoxanthopterin fluorescent nucleotide analogue"

(xi) SEQUENCE DESCRIPTION: SEQ ID NO: 60:

TAAATAANAT AGTAAGAATG TATAGCCCTA CCA                                      33

(2) INFORMATION FOR SEQ ID NO: 61:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 8
            (D) OTHER INFORMATION: /mod_base= OTHER
                /note= "N = any fluorescent nucleotide analogue"

(xi) SEQUENCE DESCRIPTION: SEQ ID NO: 61:

ACGTATGNTT CGAC                                                           14

(2) INFORMATION FOR SEQ ID NO: 62:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA
```

(xi) SEQUENCE DESCRIPTION: SEQ ID NO: 62:

TGCATACAAG CTG                                                                      13

(2) INFORMATION FOR SEQ ID NO: 63:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 9
        (D) OTHER INFORMATION: /mod_base= OTHER
            /note= "NB = any fluorescent nucleotide analogue"

(xi) SEQUENCE DESCRIPTION: SEQ ID NO: 63:

ACGTATGCNT TTCGAC                                                                   16

(2) INFORMATION FOR SEQ ID NO: 64:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 12
        (D) OTHER INFORMATION: /mod_base= OTHER
            /note= "N = any fluorescent nucleotide analogue"

(xi) SEQUENCE DESCRIPTION: SEQ ID NO: 64:

ACGTATGCTT CNTAAGTTCG AC                                                            22

(2) INFORMATION FOR SEQ ID NO: 65:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 65:

TGCATACAAA GCTG                                                                     14

(2) INFORMATION FOR SEQ ID NO: 66:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: modified_base
        (B) LOCATION: 14
        (D) OTHER INFORMATION: /mod_base= OTHER
            /note= "N = any fluorescent nucleotide analogue"

(xi) SEQUENCE DESCRIPTION: SEQ ID NO: 66:

-continued

```
ACGTATGAGC TTCNTAAGCT TTCGAC                                              26

(2) INFORMATION FOR SEQ ID NO: 67:

(i) SEQUENCE CHARACTERISTICS:
        (A) LENGTH: 22 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: modified_base
        (B) LOCATION: 16
        (D) OTHER INFORMATION: /mod_base= OTHER
              /note= "N = any fluorescent nucleotide analogue"

(xi) SEQUENCE DESCRIPTION: SEQ ID NO: 67:

ACGTATGTTC GACATNCAGT CG                                                  22

(2) INFORMATION FOR SEQ ID NO: 68:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 68:

TGCATACAA                                                                  9
```